(12) United States Patent
Rosenbaum et al.

(10) Patent No.: US 12,708,534 B2
(45) Date of Patent: Aug. 18, 2026

(54) VASCULAR STENT WITH ADJUSTABLE RADIAL STRENGTH

(71) Applicant: Cobra Neurovascular LLC, Traverse City, MI (US)

(72) Inventors: David Rosenbaum, Traverse City, MI (US); James E. Kemler, Glen Arbor, MI (US)

(73) Assignee: Cobra Neurovascular, LLC, Traverse City, MI (US)

( * ) Notice: Subject to any disclaimer, the term of this patent is extended or adjusted under 35 U.S.C. 154(b) by 0 days.

(21) Appl. No.: 19/238,757

(22) Filed: Jun. 16, 2025

(65) Prior Publication Data

US 2025/0381049 A1 Dec. 18, 2025

Related U.S. Application Data

(60) Provisional application No. 63/660,276, filed on Jun. 14, 2024.

(51) Int. Cl.
*A61F 2/95* (2013.01)
*A61B 17/12* (2006.01)
(Continued)

(52) U.S. Cl.
CPC ................ *A61F 2/95* (2013.01); *A61F 2/852* (2013.01); *A61B 2017/1209* (2013.01);
(Continued)

(58) Field of Classification Search
CPC ...... A61F 2/95; A61F 2/852; A61F 2002/828; A61F 2002/9505; A61F 2002/9528;
(Continued)

(56) References Cited

U.S. PATENT DOCUMENTS

| | | | |
|---|---|---|---|
| 6,579,308 | B1 | 6/2003 | Jansen et al. |
| 6,585,758 | B1 | 7/2003 | Chouinard et al. |

(Continued)

OTHER PUBLICATIONS

International Search Report and Written Opinion dated Sep. 19, 2025 re PCT/US2025/033711 (12 pages).

*Primary Examiner* — Melanie R Tyson
*Assistant Examiner* — Rachel S Highland
(74) *Attorney, Agent, or Firm* — Aurora Consulting LLC; Albert Du; Ashley Sloat

(57) ABSTRACT

An intravascular device may have a first configuration during deployment and a second configuration after deployment. The first configuration has a first radial strength; and the second configuration has a second radial strength. The first radial strength is less than the second radial strength. A system may include an intravascular device; a wire extending through the intravascular device to expand or contract the intravascular device; a proximal hub coupled to the wire; a distal hub coupled to the wire; and a plurality of tethers extending from an input device and through the intravascular device. At least a portion of the plurality of tethers has electrical conductivity. Application of energy to the at least a portion of the plurality of tethers may disengage the plurality of tethers from the intravascular device and fuse a luminal segment of the plurality of tethers, extending through the intravascular device, to the intravascular device.

20 Claims, 19 Drawing Sheets

(51) Int. Cl.
*A61F 2/82* (2013.01)
*A61F 2/852* (2013.01)

(52) U.S. Cl.
CPC ..... *A61B 17/12118* (2013.01); *A61B 17/1214* (2013.01); *A61F 2002/828* (2013.01); *A61F 2002/9505* (2013.01); *A61F 2002/9511* (2013.01); *A61F 2002/9528* (2013.01); *A61F 2250/0004* (2013.01)

(58) Field of Classification Search
CPC ..... A61F 2250/0004; A61F 2002/9511; A61B 17/12118; A61B 17/1214; A61B 2017/1209
See application file for complete search history.

(56) References Cited

U.S. PATENT DOCUMENTS 6,716,238 B2 4/2004 Elliott
7,001,425 B2 2/2006 McCullagh et al.
9,439,791 B2 9/2016 Vong et al.
9,827,093 B2 11/2017 Cartledge et al.
9,867,725 B2 1/2018 Tieu et al.
10,561,509 B2 2/2020 Slazas et al.
11,911,305 B2 2/2024 Smith et al.
12,349,929 B2 7/2025 Sudin et al.
2001/0047150 A1* 11/2001 Chobotov ................. A61F 2/07 604/107
2002/0188341 A1* 12/2002 Elliott ..................... A61F 2/958 623/1.1
2010/0010619 A1* 1/2010 Tischler .................... A61F 2/95 623/1.16
2010/0049302 A1 2/2010 Kang et al.
2010/0268204 A1* 10/2010 Tieu .......................... A61F 2/01 606/108
2011/0029062 A1 2/2011 Kang
2014/0163664 A1* 6/2014 Goldsmith ......... A61B 17/0057 604/93.01
2017/0290686 A1 10/2017 Sirhan et al.
2018/0311058 A1 11/2018 Mannion et al.
2023/0118855 A1 4/2023 Gifford, III et al.
2023/0201014 A1 6/2023 Sirhan et al.

* cited by examiner

VASCULAR STENT WITH ADJUSTABLE RADIAL STRENGTH

CROSS-REFERENCE TO RELATED APPLICATIONS

This application claims the priority benefit of U.S. Provisional Patent Application Ser. No. 63/660,276, filed Jun. 14, 2024, the contents of which is herein incorporated by reference in its entirety.

TECHNICAL FIELD

This disclosure relates generally to the field of medical device implants, and more specifically to the field of vascular or neurovasculature stenting. Vascular stents having an adjustable radial strength are described herein.

BACKGROUND

Neurovascular stenting is a medical procedure used to treat narrowed or blocked blood vessels within the neurovasculature. Neurovascular stenting is often performed to restore blood flow to the affected area and reduce the risk of complications such as strokes or aneurysms.

Neurovascular stenting can be used to treat conditions such as intracranial atherosclerosis (i.e., narrowing of intracranial blood vessels due to plaque buildup), carotid artery stenosis (i.e., narrowing of the carotid arteries in the neck), and other vascular abnormalities affecting the nervous system. It is often considered a minimally invasive alternative to traditional open surgery and can help reduce recovery time and complications for patients.

SUMMARY

In some aspects, the techniques described herein relate to an intravascular device including: an outer stent and a support structure that is at least partially disposed in of the outer stent; the lumen is configured to have: a first configuration during deployment, wherein the first configuration has a first radial strength; and a second configuration after the deployment, wherein the second configuration has a second radial strength and the support structure is fused, at a plurality of fusion points, to the lumen of the outer stent by applying energy to the intravascular device, the fusion fixing a diameter of the intravascular device in the second configuration, wherein the first radial strength is less than the second radial strength.

In some aspects, the techniques described herein relate to an intravascular device including: a stent having a proximal end, a distal end, and a lumen therethrough; a wire configured to extend through the lumen and expand or contract the stent responsive to manipulation of the wire; a proximal hub slidably coupled to a proximal region of the wire; a distal hub coupled to a distal region of the wire; and a plurality of tethers configured to extend from an input device to the proximal hub and to the proximal end of the stent, wherein the plurality of tethers is further configured to extend through the lumen and couple the distal end of the stent to the distal hub, and wherein at least a portion of the plurality of tethers has electrical conductivity; wherein application of an electric current to the at least a portion of the plurality of tethers is configured to: disengage the plurality of tethers from the proximal end and the distal end of the stent, respectively, and fuse a luminal segment of the plurality of tethers, extending through the lumen of the stent, to the stent.

In some aspects, the techniques described herein relate to a method of deploying an intravascular device, including: navigating the intravascular device to a target vasculature, the intravascular device including: an outer stent having an outer stent lumen, a support structure extending through the outer stent lumen, and a translatable wire configured to extend through the outer stent lumen and couple to the support structure; manipulating the translatable wire to cause the support structure to at least partially expand or contract the outer stent; and applying an electric current to the support structure to fuse at least a portion of the support structure to the outer stent at a plurality of fusion points along the outer stent lumen and to disengage the support structure from the translatable wire.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
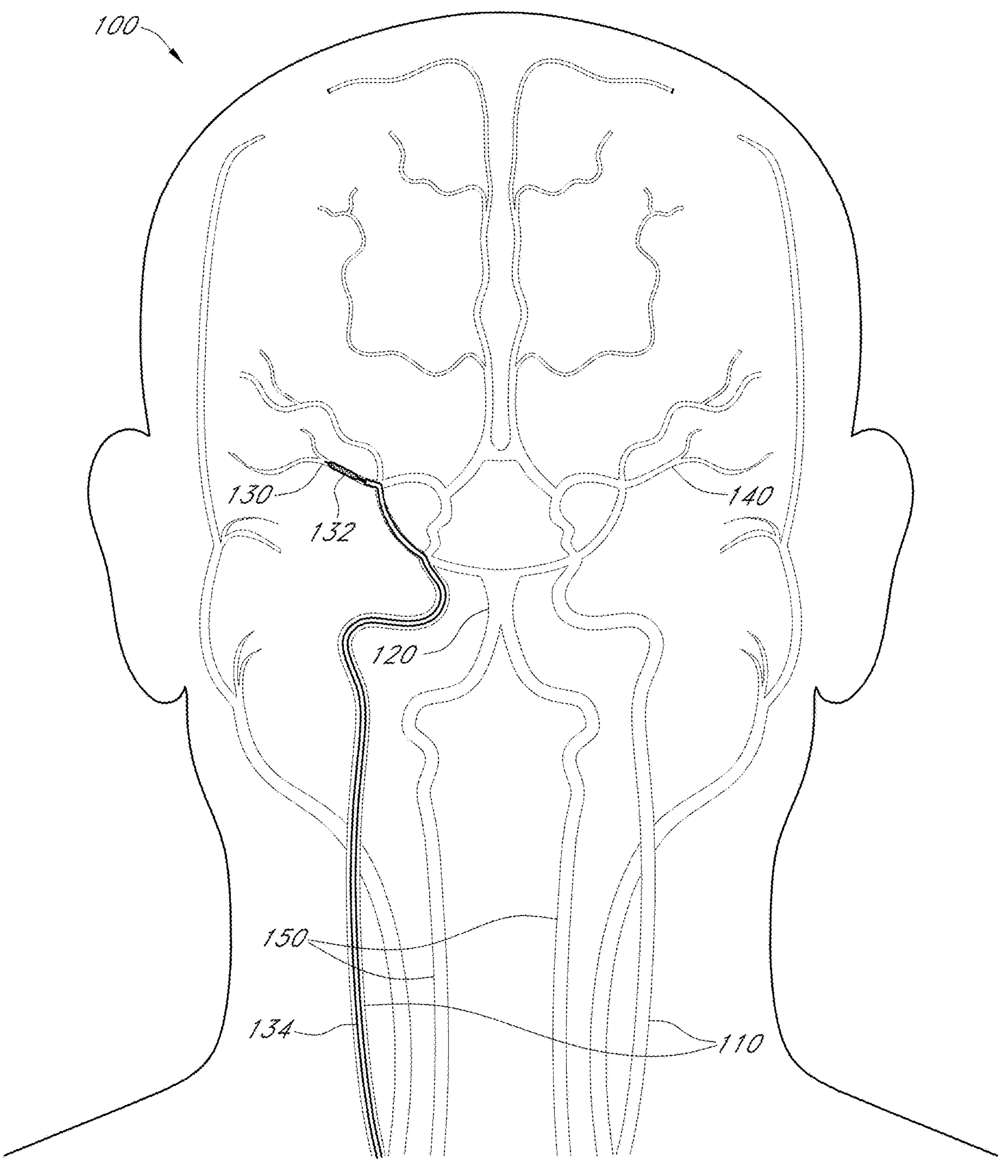
FIG. 1 shows an embodiment of an intravascular device deployed in a middle cerebral artery of a patient.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The neurovasculature or intracranial vasculature is tortuous, which results in several technical challenges in using and deploying conventional stents. For example, conventional self-expanding stents, balloon expandable stents, and/or braided wire stents are non-compliant and stiff. As such, conventional self-expanding stents, balloon expandable stents, and/or braided wire stents can be difficult to navigate through and deploy within the intracranial vasculature. For example, balloon expandable stents may stretch or distort the anatomy since the expanded diameter is not tunable. Further, self-expanding stents and balloon expandable stents are size-selected for the target anatomy since the expanded diameter of the self-expanding stents is restricted by the target anatomy or dictated by balloon expansion. As such, the radial strength of conventional stents may be predetermined based on the stent material or the balloon expansion.

Another technical challenge (e.g., technical problem) is that self-expanding stents and/or balloon expandable stents are difficult to recapture or reposition. To reposition a non-balloon mounted implant, the deployed, partially expanded implant may be re-catheterized with the balloon post deployment. Re-catheterization can result in movement, distention, and/or kinking of the implant. The balloon, when re-deployed, can cause the implant to move, as well as cause blood vessel injury.

The intravascular devices and methods described herein overcome the above technical challenges with technical solutions. The technical solutions provided by the intravascular devices and methods described herein include providing an intravascular device that is compliant and easily navigable in the anatomy. The intravascular device may have an initially low radial strength (e.g., between about 0 N to about 0.5 N). The intravascular device may include an inner stent (or scaffold) disposed within a lumen of, and coupled to, an outer stent. In some embodiments, the inner stent (or scaffold) may be fully disposed within a lumen of an outer stent. In some embodiments, the inner stent (or scaffold) may be partially disposed within a lumen of an outer stent. In some embodiments, the inner stent (or scaffold) may be at least partially disposed within a lumen of an outer stent. Once the intravascular device is positioned in the target vasculature, the inner stent (or scaffold), extending through the lumen of the outer stent of the intravascular device, may be fused, at least partially, to the outer stent. The fusion of the inner stent (or scaffold) to the outer stent can set (e.g., fix the radial strength) the radial strength of the combined outer stent and inner stent (or scaffold), which is greater than the initial radial strength of the unfused inner and outer stents. For example, setting or fixing the radial strength may include fixedly coupling the inner stent to the outer stent, for example by bonding, melting, fusing, etc., the inner stent to the outer stent so that they together form an intravascular device with a particular radial strength. In a further technical solution, the intravascular devices described herein can be retrieved or repositioned before fusion of the inner stent (or scaffold) to the outer stent and/or before dissociation of the intravascular device from the delivery system.

Having a radial strength that is not correctly sized for the application or the target vasculature can be detrimental in that the device may fail to function. Further, an implant having an unexpectedly high radial strength can result in complications such as in-stent stenosis, an increased inflammatory response, or thrombosis. In contrast, an implant having an unexpectedly low radial strength can lead to poor support of the target vasculature, poor treatment of the target vasculature, an increase in the risk of thrombosis, and/or implant migration in the vessel. The intravascular devices and methods described herein solve the aforementioned technical problems with technical solutions. The intravascular devices described herein provide for a tunable radial strength. For example, the intravascular devices described herein in an unexpanded configuration may have a low initial radial strength, for easy tracking through the vasculature. Once positioned in the target anatomy, the intravascular device may be expanded (e.g., to substantially match a diameter of the target anatomy, to expand the target anatomy, to jail off a branch vessel, to jail off an aneurysm neck, etc.) and an inner stent (or scaffold) of the intravascular device may be fused to an outer stent of the intravascular device to set the radial strength of the expanded intravascular device. The inner stent may be at least partially fused to the outer stent. The inner stent may be fully fused to the outer stent. The radial strength of the expanded intravascular device (with inner and outer stents fused) may be greater than the initial radial strength of the intravascular device before fusion. The devices described herein may provide a technical benefit of improving deployment success using a lesser radial strength in a first arrangement (for easier tracking through tortuous vasculature) and providing for a stronger radial strength when in a second and deployed arrangement to improve device compliance (and/or radial strength) to a number of different shaped (or sized) anatomy.

A further technical problem of conventional implants is that conventional implants (e.g., self-expanding stents, balloon expandable stents, and/or braided wire stents) are designed in preset sizes. As such, the manufacturer may produce implants in multiple different diameters and lengths. The intravascular devices described herein solve this technical problem with a technical solution including enabling the intravascular devices described herein to be adjusted in-situ to an appropriate diameter in real time. For example, proximal retraction of the translatable wire of the intravascular device can cause expansion of the intravascular device. The amount of proximal retraction can be varied depending on the target vasculature (e.g., diameter, tortuosity, state of the vasculature (i.e., plaque present), etc.). Said another way, the outer stent may be passively expanded and contracted by manipulation of the inner stent (or scaffold) by the translatable wire. Once the desired diameter of the intravascular device is achieved, the inner stent can be fused, at least partially, to the outer stent to set or fix the diameter of the expanded intravascular device.

The inner stent fusion to the outer stent may be achieved through the application of energy. For example, the energy may be electric current, heat, ultrasonic energy, etc. In some embodiments, electrical energy may be applied to the intravascular device through the delivery system to fuse the inner stent to the outer stent and to disengage the intravascular device from the delivery system. For example, by disengaging the fused outer stent and inner stent from the translatable wire. The electrical energy (alternating current or direct current) may be in a range of about 0.05 mA to about 3 mA; about 1 mA to about 2 mA; about 0.05 mA to about 1 mA; about 1.5 mA to about 2 mA; about 2 mA to about 2.5 mA; about 2.5 mA to about 3 mA; etc. In some embodiments, a first pulse of energy may be applied to fuse the inner stent to the outer stent. In some embodiments, a second pulse of energy may be applied to disengage the intravascular device from the delivery system. In some embodiments, a pulse of energy may be applied to fuse the inner stent to the outer stent and disengage the intravascular device from the delivery system.

In some embodiments, the intravascular devices described herein are sized and/or shaped to be deployed though a catheter or a microcatheter. For example, the intravascular devices described herein may have a crimped diameter of about 0.015 in. (0.381 mm) to about 0.025 in. (0.635 mm); about 0.015 in. (0.381 mm) to about 0.020 in. (0.508 mm); about 0.020 in. (0.508 mm) to about 0.025 in. (0.635 mm); etc. to enable manipulation of the intravascular device through a lumen of a microcatheter. For example, the intravascular devices described herein may have a crimped diameter of about 0.025 in. (0.635 mm) to about 0.077 in, (1.956 mm); about 0.025 in. (0.635 mm) to about 0.037 in. (0.94 mm); about 0.037 in. (0.94 mm) to about 0.051 in. (1.296); about 0.051 in. (1.296) to about 0.064 in, (1.626); about 0.064 in. (1.626) to about 0.077 in. (1.956); etc. to enable manipulation of the intravascular device through a lumen of a catheter.

In some embodiments, the intravascular devices described herein, or an inner stent and/or outer stent of the intravascular devices, may include an anti-thrombotic coating and/or a drug eluting coating. In some embodiments, the intravascular devices described herein, or an inner stent and/or outer stent of the intravascular devices, may include a material impregnated with an anti-thrombotic material, chemical, or drug. The coating, material, and/or drug may reduce thrombosis and/or hyperplasia. Exemplary, non-limiting examples of anti-thrombotic coatings applied to the devices described herein include heparin, hyaluronic acid, endothelial progenitor cell capturing coatings, phosphorylcholine, nitric oxide releasing coatings, etc. Exemplary, non-limiting examples of drugs that could be included in drug-eluting coatings applied to the devices described herein include Sirolimus, Paclitaxel, Everolimus, Zotarolimus, epoxy-based polymers, Biolimus A9, etc.

As used herein, “proximal” means near or toward an operator of the device and “distal” means away from the operator and toward a patient or target vasculature in which the intravascular device is inserted. Distal end 204 and proximal end 202 are further labeled in FIG. 2 for the sake of clarity but are understood to apply to all the embodiments described herein.

As used herein, “inner stent,” “scaffold,” “support structure,” and “luminal segment” may be used. The terms generally describe a structure that is disposed (e.g., fully, partially, at least partially, etc.) in a lumen of, and coupled to, an outer stent. The structure may be manipulatable by a translatable wire to cause expansion or contraction of the outer stent.

As used herein, “dissociate” or “disengage” may include, be described as, or be understood to include lysing, breaking, disrupting, cleaving, etc. or otherwise disconnecting a first element from a second element, or many first elements from one or more second elements.

As used herein, “fusing” or “altering” may include, be described as, or be understood to include melting, polymerizing, bonding, welding, or otherwise connecting or coupling a first element to a second element, or many first elements to one or more second elements.

FIG. 1 shows an intravascular device 132 deployed, through catheter 134, in a right middle cerebral artery 130 of a patient 100. As shown in FIG. 1, the intracranial vasculature includes internal carotid arteries 110, basilar artery 120, right middle cerebral artery 130, left middle cerebral artery 140, intracranial vertebral arteries 150, and common carotid arteries 160, among others. Although the intravascular device 132 is shown as deployed in the middle cerebral artery 130, the intravascular device 132 may, alternatively, be deployed in any of the basilar artery 120, internal carotid artery 110, left middle cerebral artery 140, intracranial vertebral arteries 150, or common carotid arteries 160. Further, the intravascular device 132 may be adapted for other neurovasculature or vasculature outside of the neuroanatomy, for example peripheral vasculature. Adapting may include adjusting a crimped and/or expanded diameter of the intravascular device, a length of the intravascular device, an intravascular device structure (e.g., cell structure, number of rings, number of bridges, intravascular device material, number of crowns, etc.), or any other parameter that may affect a target anatomy. The intravascular device 132 may be deployed in a target vasculature to treat intracranial atherosclerosis, carotid artery stenosis, internal carotid artery disease, or other vascular abnormalities affecting the nervous system.

The intravascular device 132 may include a lumen and have a first configuration during deployment and a second configuration after the deployment. The first configuration may have a first radial strength, for example from about 0 N to about 0.5 N. The second configuration may have a second radial strength, for example from about 1.0 N to about 3.0 N. For example, when the first configuration is used, the intravascular device may be deployed into a vessel (e.g., neurovasculature); and when the second configuration is used, the intravascular device may be operating to expand a vessel (e.g., having plaque or other material therein) and/or to improve blood flow through the vessel. The first radial strength may be less than the second radial strength. In some embodiments, the intravascular device may further include a support structure disposed (e.g., fully, partially, at least partially, etc.) in the lumen of the outer stent. The second configuration may include the support structure fused into the lumen of the outer stent to cause the intravascular device to have the second radial strength. The support structure may be described herein as an inner stent or a scaffold or a luminal segment of a plurality of tethers, as described in further detail elsewhere herein.

Figure 2:
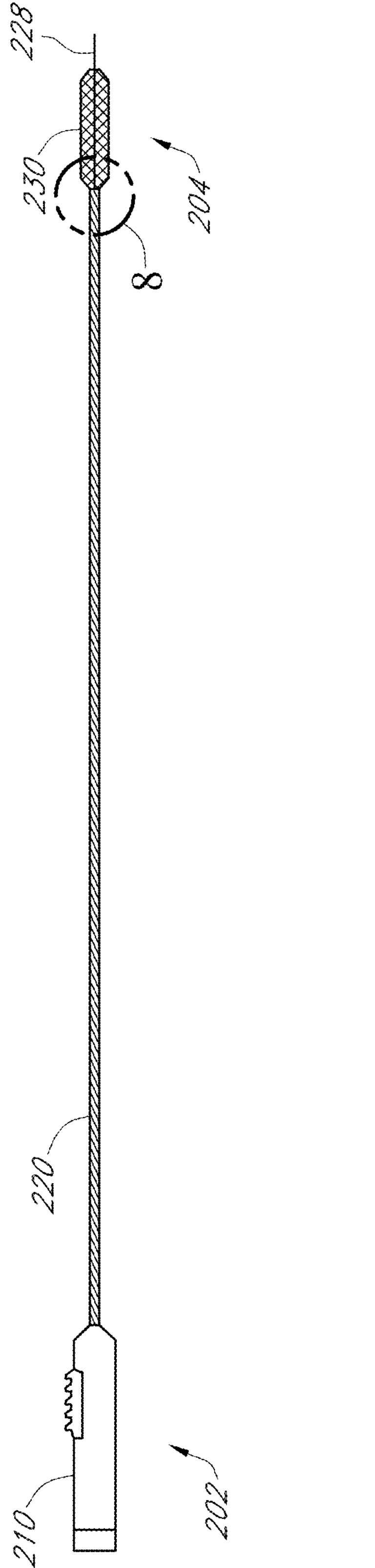
FIG. 2 shows an embodiment of an intravascular device in an expanded configuration, tethered to a delivery system.

FIG. 2 shows an intravascular device 230 in an expanded configuration, tethered to a delivery system 200. Delivery system 200 includes an input device 210. The input device 210 may be a retractor, for example as shown schematically in FIG. 3. The input device 210 is coupled to a proximal end of a plurality of tethers 220 and translatable wire 228. The plurality of tethers 220 may form a braided or wound plurality of wires, for example wound in a clockwise or counterclockwise bundle. Manipulation of translatable wire 228 by input device 210 can cause expansion or contraction of at least a portion of the intravascular device 230. For example, the input device 210 may include a graduated or stepped locking mechanism to lock the translatable wire 228 at various locations that correspond to a particular expansion diameter of the intravascular device 230. For example, the input device 210 may include a thumb wheel with a plurality of features that engage with the translatable wire 228 and adjust a position of the translatable wire 228, for example with each movement either forward or backward of the thumb wheel. In some embodiments, the wheel can be locked on the translatable wire 228 by depressing the wheel perpendicular to the translatable wire 228, which may prevent further movement of the translatable wire 228. In some embodiments, it may be unlocked by pressing the wheel again to release the lock.

Figure 3:
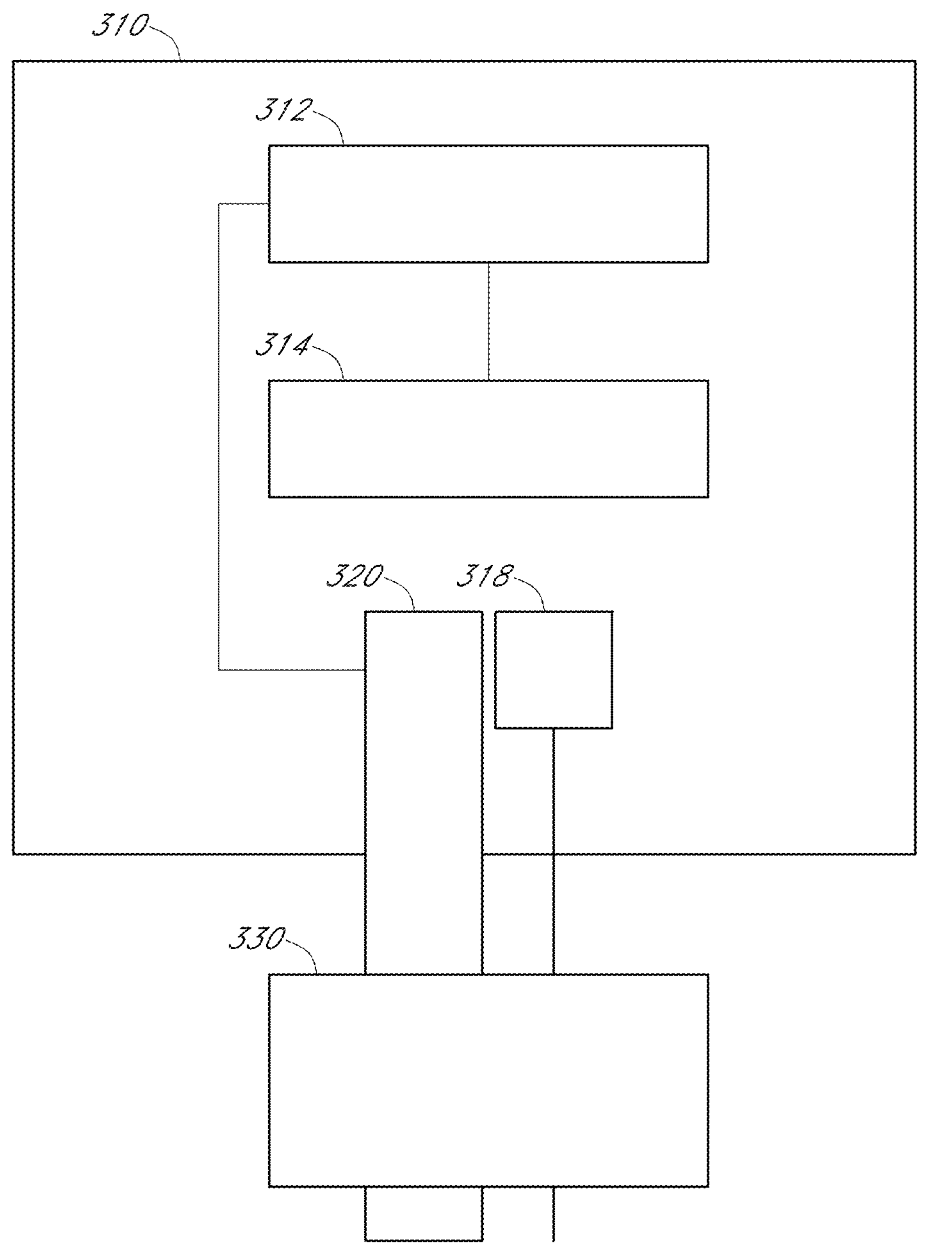
FIG. 3 shows a schematic of an embodiment of a delivery system, including an input device, and an intravascular device.

FIG. 3 shows a schematic of an embodiment of a delivery system, including an input device 310, and an intravascular device. Input device 310 includes a power source 312 and a switch 314 connected in series to a plurality of tethers 320. For example, activation of switch 314 may complete the circuit to provide electric current from power source 312 to the plurality of tethers 320. A range of about 2.5 volts to about 3.5 volts may be applied to one or more of the plurality of tethers 320 to maintain about 1 mA of current to achieve detachment of the plurality of tethers 320 from the intravascular device 330, but other voltage ranges may be used depending on the materials utilized in the intravascular device 330. For example, the voltage used to detach the plurality of tethers 320 from the intravascular device 330 may depend on the number of tethers, the thickness of each tether, the resistance of the material of the tethers, etc. The current passes through the tether(s) 320 and exits through a grounding patch, which is connected to ground via an electrode. The power source 312 may be a battery, for example a rechargeable battery or single use battery. The power source 312, for example, may be a 9 V battery, 12 V battery, etc. The input device 310 may further include an input element 318. The input element 318 may be a slider, button, dial, or other control etc. that can manipulate the translatable wire 328 to expand or contract the intravascular device 330. The input element 318, when activated or selected, may interact with a locking mechanism to lock the translatable wire 328 at one or more locations along the translatable wire 328 that correspond to a particular expansion diameter of the intravascular device 330. Although one or more locations along the translatable wire 328 are described, one of skill in the art will appreciate that there may be an infinite number of locations such that the translatable wire 328 may be locked anywhere along its length.

FIGS. 4-7 show various stages of delivery of an intravascular device and example delivery systems 400, 500, 600, or 700. In general, the intravascular devices described herein may be delivered to a target vasculature to treat a vascular abnormality, internal carotid intracranial atherosclerosis, or carotid artery stenosis.

Figure 4:
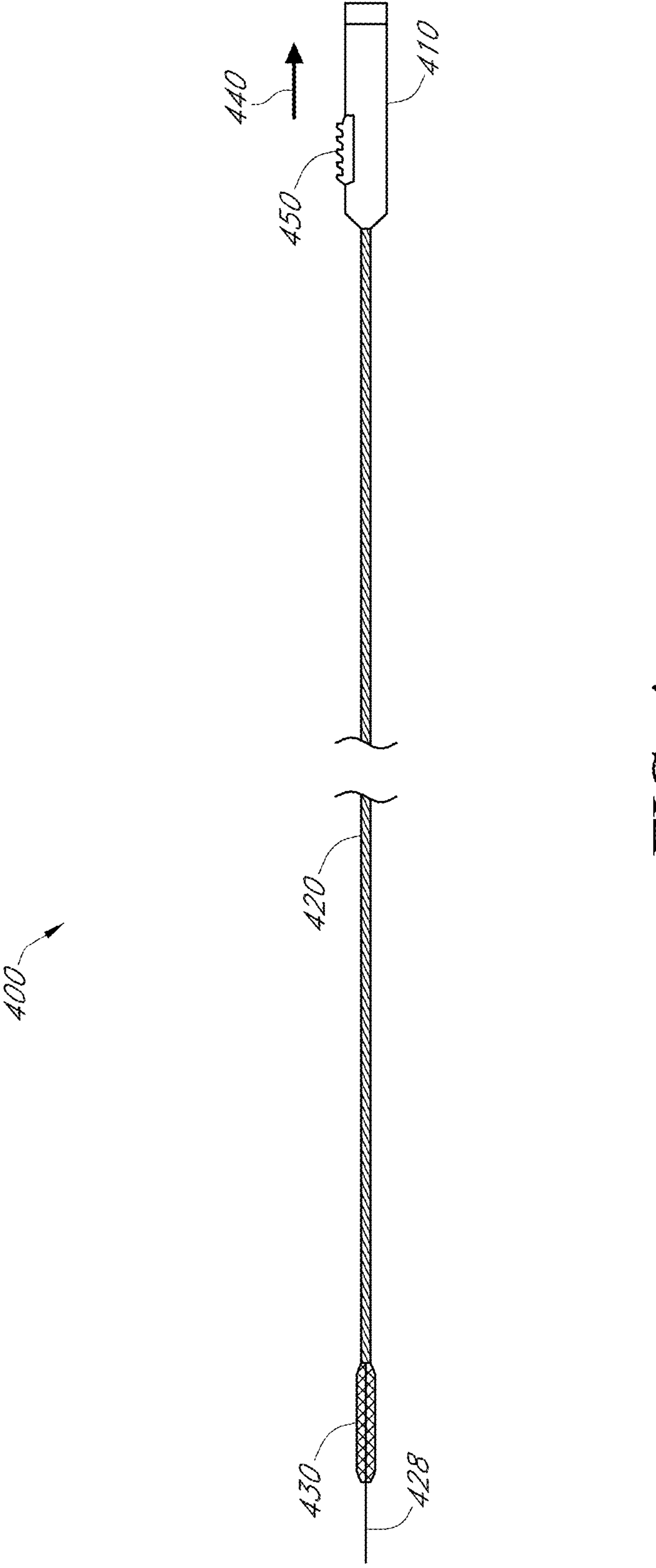
FIG. 4 shows an embodiment of an intravascular device in an unexpanded configuration, tethered to a delivery system.

FIG. 4 shows an intravascular device 430 in an unexpanded or contracted configuration, tethered to a delivery system 400. The delivery system 400 includes an input device 410, as described in FIG. 3. The input element 450 of the input device 410 may be manipulated to apply a force 440 to the translatable wire 428 to expand or retract the intravascular device 430. Although the applied force 440 (e.g., about 0.05 N to about 0.3 N) is shown in a proximal direction, for example to expand the intravascular device 430, it will be appreciated that the applied force may be in a distal direction, for example to collapse or contract or reposition the intravascular device 430. Axial translation of the translatable wire 428 may be improved or aided by insulation material encapsulating the translatable wire 428. The insulation material may have a particular lubricity, for example, to improve translation.

Figure 5:
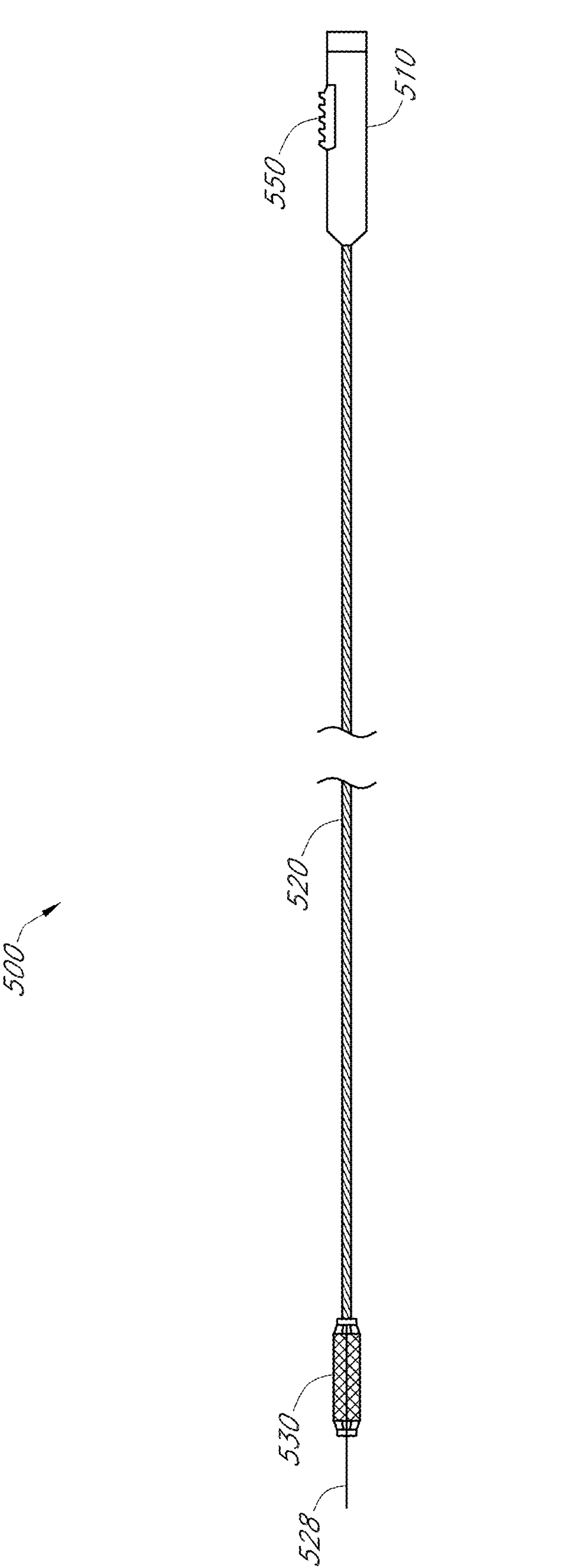
FIG. 5 shows an embodiment of an intravascular device in an expanded configuration, tethered to a delivery system.

FIG. 5 shows an intravascular device 530 in an expanded configuration, tethered to a delivery system 500. Manipulation of the input element 550 of the input device 510 of the delivery system 500 causes axial translation of translatable wire 528 to cause expansion of the intravascular device 530 (e.g., via force 440). As described elsewhere herein, although tether 520 is shown as a single tether, tether may include a plurality of tethers wound around the translatable wire 528. For example, the wound plurality of tethers 520 may form a lumen through which translatable wire 528 translates. Axial translation of translatable wire 528 may cause compression (translation of the translatable wire proximally) or decompression (translation of the translatable wire distally) of the plurality of tethers 520. In some embodiments, the compression is longitudinal compression along longitudinal axis L shown in FIG. 9A.

Figure 6:
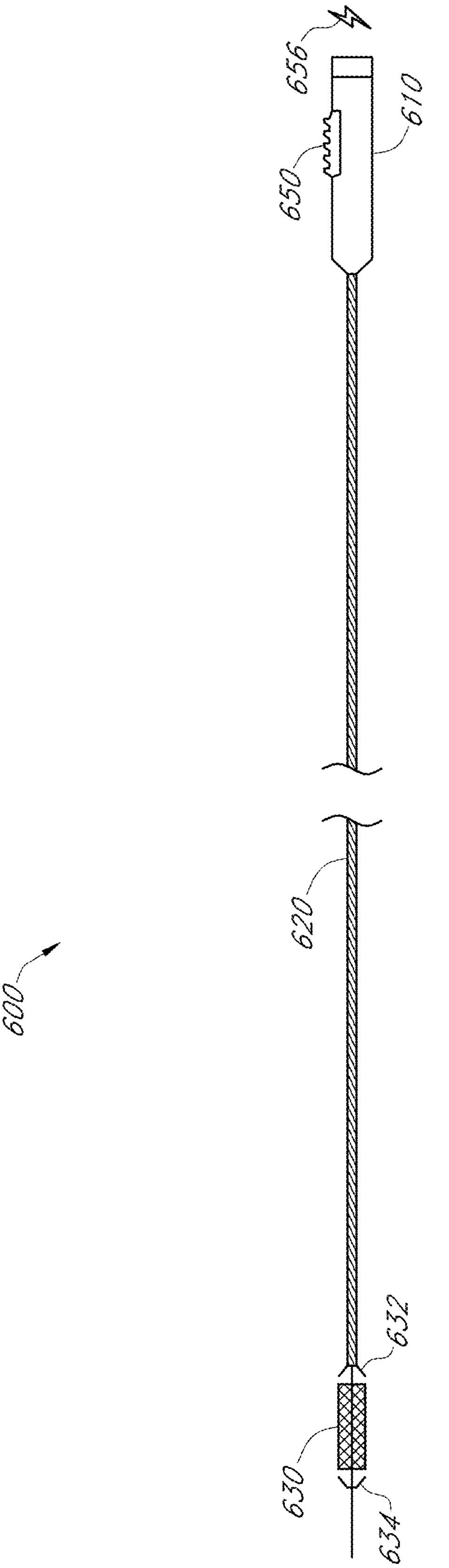
FIG. 6 shows an embodiment of an intravascular device in an expanded configuration and untethered from a delivery system.

FIG. 6 shows an intravascular device 630 in an expanded configuration and untethered to a delivery system 600. The delivery system 600 includes the input device 610 and switch 650. Switch 650 may be triggered e.g., activated (shown by bolt 656) to complete the circuit to allow current from the power source (shown in FIG. 3) to travel along one or more of the plurality of tethers 620 until the current reaches an uninsulated section (e.g., bare wire or bare material) of one or more of the plurality of tethers 620. The uninsulated section may be where the plurality of tethers 620 connects to a proximal end and/or a distal end of the intravascular device 630 and/or along a plurality of portions of a luminal segment of the plurality of tethers 620 that is disposed (e.g., fully, partially, at least partially, etc.) in a lumen of an outer stent of the intravascular device 630. Activation of the switch 650 may cause disengagement of the plurality of tethers 620 from the proximal end and/or distal end of the intravascular device and/or fusion of the luminal segment of the plurality of tethers 620 with the outer stent of intravascular device 630.

Activation of the switch 650 may break or disconnect the proximal plurality of tethers 632 from the intravascular device 630 and/or the distal plurality of tethers 634 from the intravascular device 630. The breaking or disconnecting may release the intravascular device 630 from the plurality of tethers 620 and the translatable wire 628. The breaking or disconnecting may further fuse the support structure (i.e., luminal segment) to the outer stent, as will be described in further detail elsewhere herein.

Figure 7:
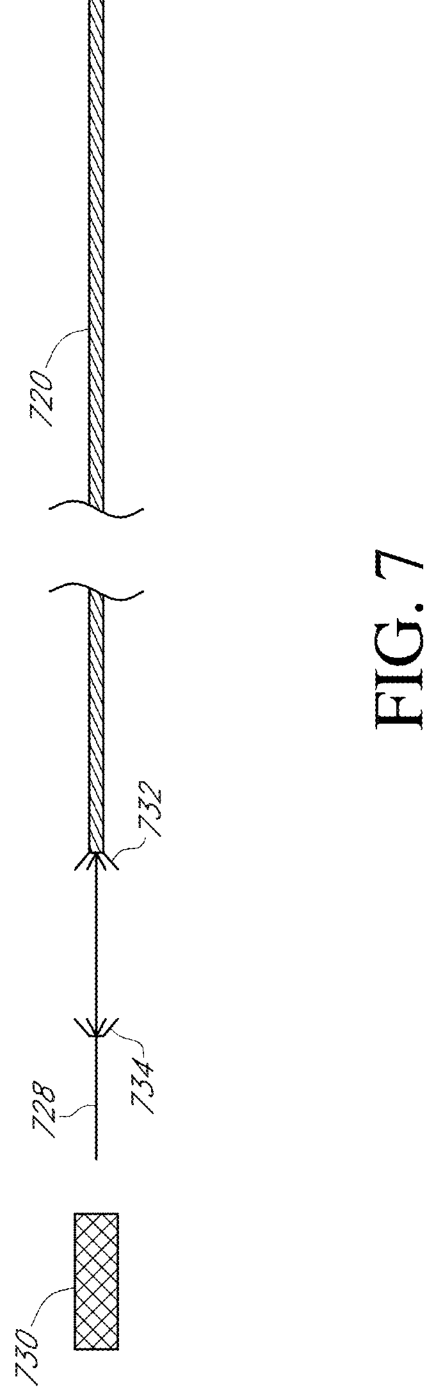
FIG. 7 shows an embodiment of a proximal retraction and removal of a delivery system.

FIG. 7 shows proximal retraction and removal of a delivery system 700. With the proximal plurality of tethers 732 and a distal plurality of tethers 734 released (e.g., through application of electric current) from the intravascular device 730, the plurality of tethers 720 including the plurality of tethers 732, 734, and the translatable wire 728 can be removed from the vasculature.

FIGS. 8A-14 show various features and structures of an embodiment of the intravascular device and how the intravascular device relates to the delivery system.

Figure 8A:
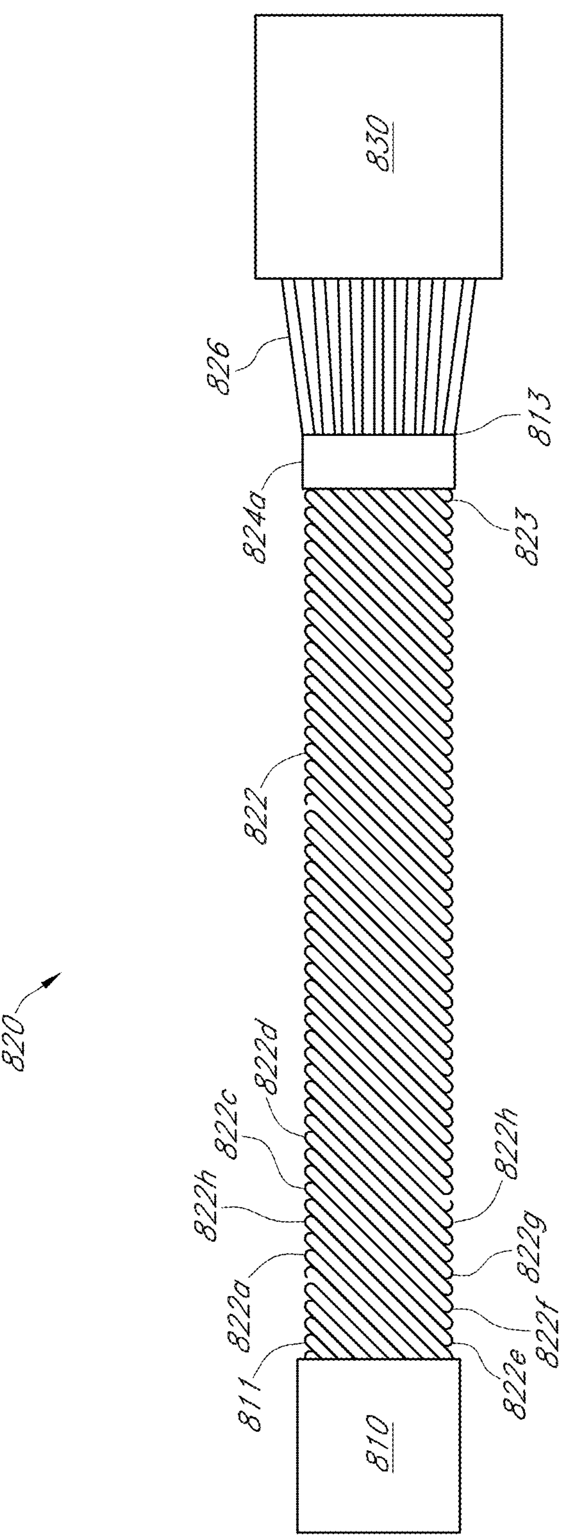
FIG. 8A shows a zoomed-in view of an embodiment of a proximal portion of a plurality of tethers and a proximal hub of a delivery system.
Figure 9A:
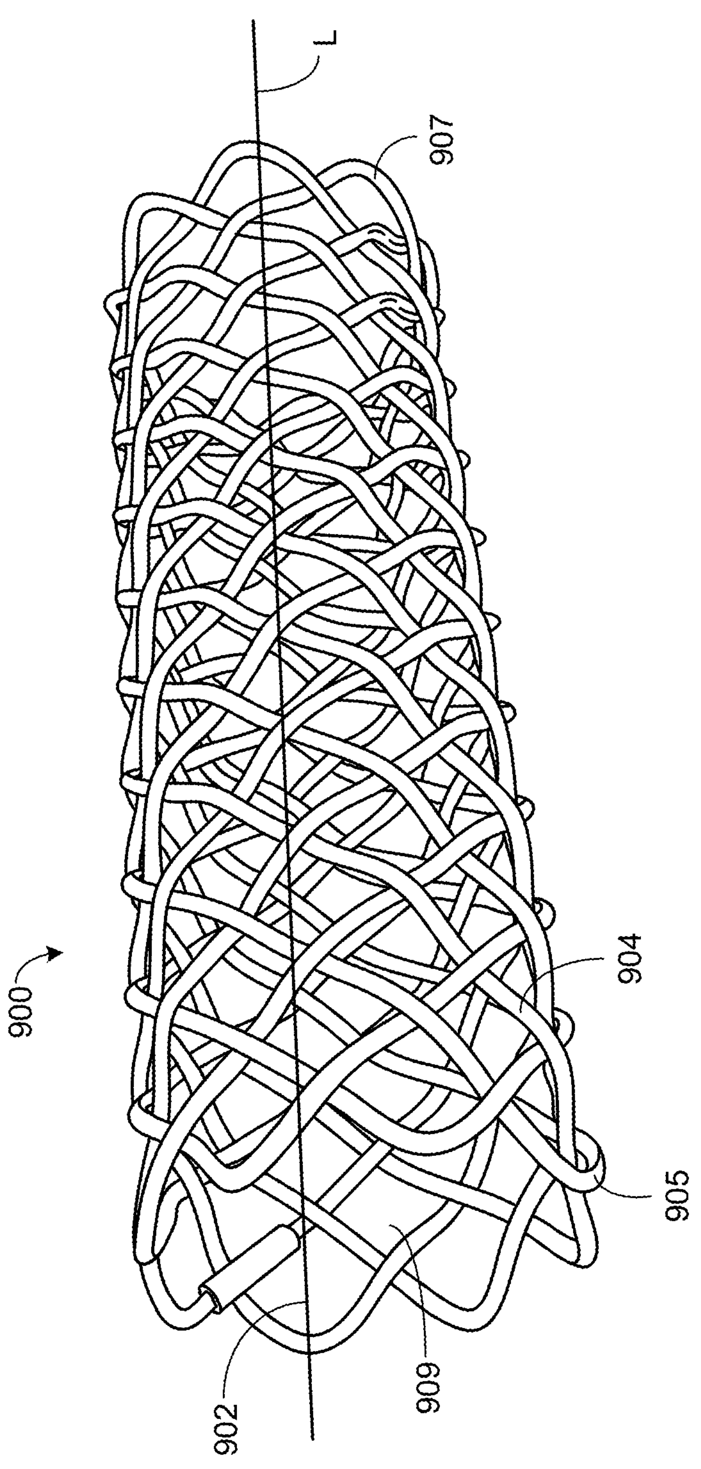
FIG. 9A shows a perspective view of an embodiment of an outer stent of an intravascular device.
Figure 9A:
Figure 9B:
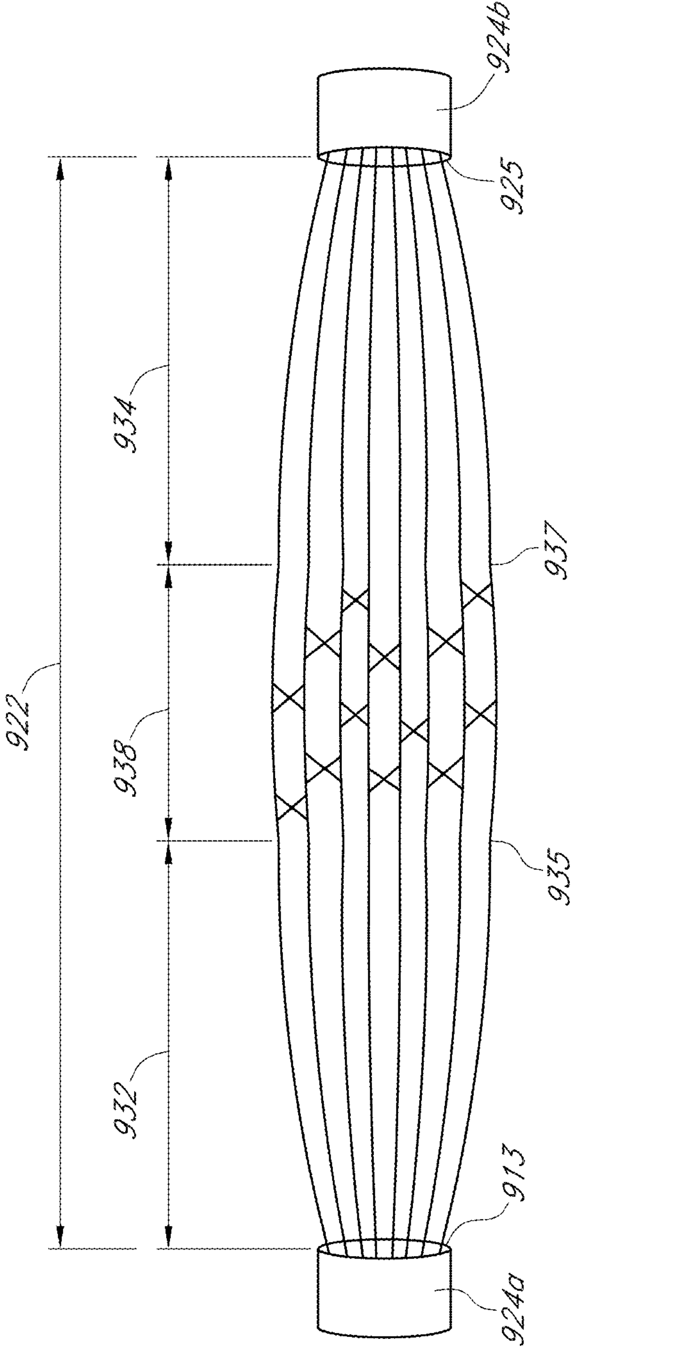
FIG. 9B shows an embodiment of a scaffold formed from a plurality of tethers that pass through or are coupled to the proximal hub and the distal hub, respectively.

FIG. 8A shows a zoomed-in view of a proximal portion of the plurality of tethers 820 and a proximal hub 824*a* of a delivery system. The plurality of tethers 820 may be continuous from the input device 810 to the proximal hub 824*a* and the distal hub (shown in FIGS. 9A-9B as 924*b*), such that the plurality of tethers 820 connects to, and passes through a lumen of, the intravascular device 830 (as shown in FIGS. 9A-9B). One of skill in the art will appreciate that the proximal portion of the plurality of tethers 820, shown in FIG. 8A, is shown in a truncated length format to illustrate various features of the delivery system. For example, the plurality of tethers 820 may have a length between about 100 cm to about 160 cm; about 100 cm to about 140 cm; about 115 cm to about 160 cm; about 130 cm to about 160 cm; etc. In some embodiments, the plurality of tethers 820 may include a plurality of braided tethers 822. For example, there may be about eight tethers, tether 822*a*, tether 822*b*, tether 822*c*, tether 822*d*, tether 822*e*, tether 822*f*, tether 822*g*, tether 822*h*. Although eight tethers are shown, one of skill in the art will appreciate that any number of tethers may function for the intended purpose. For example, there may be about one tether to about five tethers, about two tethers to about ten tethers, about four tethers to about eight tethers, etc. The plurality of tethers 822 can be wound in a clockwise or counterclockwise direction about the translatable wire 828 such that axial translation (e.g., advancement or retraction) of the translatable wire 828 to expand or contract the intravascular device may cause compression (or contraction) or decompression (or elongation), respectively, of the plurality of tethers 822 (the proximal end 811 of the tethers 822 being fixedly coupled to the input device 810, and the distal end 823 of the tethers 822 being coupled to the proximal hub 824*a*). Said another way, the plurality of tethers 822 may form a lumen through which the translatable wire 828 can axially translate. The proximal hub 824*a* may be slidably coupled to a proximal region of the translatable wire 828 (i.e., slide along the proximal region of the translatable wire 828) and the proximal hub 824*a* may be disposed on a distal end 823 of the plurality of tethers 822. The plurality of tethers 822 straighten at the proximal hub 824*a*, resulting in the plurality of tethers 826. In some embodiments, the plurality of tethers 822 are the same as the plurality of tethers 826 (as shown in FIGS. 9A-9B), since the plurality of tethers 822 pass through the proximal hub 824*a* and are straightened on the opposite side (i.e., the distal side 813) of the proximal hub 824*a* resulting in the plurality of tethers 826. In some embodiments, the plurality of tethers 822 are different from the plurality of tethers 826, such that the plurality of tethers 822 is coupled to a proximal side 823 of the proximal hub 824*a* and a proximal end of the plurality of tethers 826 is coupled to an opposite side of the proximal hub 824*a*.

Figure 8B:
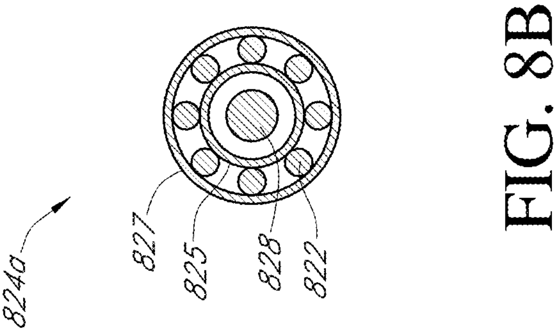
FIG. 8B shows a cross-sectional view of an embodiment of a proximal hub of a delivery system.

FIG. 8B shows a cross-sectional view of a proximal hub 824*a* of a delivery system. The proximal hub 824*a* defines a lumen 825 through which the translatable wire 828 axially translates. Said another way, the proximal hub 824*a* may axially translate along the translatable wire 828 and can cause compression or decompression of the plurality of tethers 822. When the intravascular device 830 is expanded, the translatable wire 828 may be pulled proximally (via the input device 810), such that the input device 810 is a back stop to the plurality of tethers 822, causing compression of the plurality of tethers 822. When the intravascular device 830 is contracted or expansion of the intravascular device 830 is reduced, the translatable wire 828 may be pushed distally (via the input device 810), such that the distal hub (which is coupled to a distal region of the translatable wire 828 and not axially translatable along the translatable wire 828) is a limit during contraction of the intravascular device 830, therefore causing decompression of the plurality of tethers 822.

As shown in FIG. 8B, the translatable wire 828 may be at least partially disposed within the proximal hub 824*a*. For example, the translatable wire 828 may pass through a lumen 825 of the proximal hub 824*a*. The lumen 825 may partially circumferentially enclose the translatable wire 828. Alternatively, the lumen 825 may fully circumferentially enclose the translatable wire 828. The plurality of tethers 822 may be coupled to and/or pass through the proximal hub 824*a*, for example between the lumen 825 and an exterior surface 827 of the proximal hub 824*a*. The plurality of tethers 826, on the distal side 813 of the proximal hub 824*a*, may be substantially parallel to the translatable wire 828 when the intravascular device 830 is in an undeployed or unexpanded configuration. The plurality of tethers 826, on the distal side 813 of the proximal hub 824*a*, may radially extend from the proximal hub 824*a* and couple to a proximal end of the outer stent 900 (shown in FIG. 9A) of intravascular device 830. The insulation of the plurality of tethers 822, 826 of FIG. 8A may cease at the coupling or interface between the plurality of tethers 826 and the proximal end (and/or distal end) of the intravascular device 830. The intravascular device 830 may be insulated such that the outer stent 900 (shown in FIG. 9A), when formed of a polymer or other non-conductive material, may provide insulation from the electric current when the inner stent is fused to the outer stent to form the intravascular device 830.

FIGS. 9A-9B show an outer stent and a support structure, coupled to a plurality of tethers and hubs, respectively. In some embodiments, the outer stent 900 and/or inner stent 938 or support structure may have a lattice structure, a diamond seamless structure, a vector seamless structure, a seamless wavy line structure, or any other pattern or geometric shape or structure. In some embodiments, the outer stent 900 may include or be formed of a polymer, as shown in FIG. 9A. In some embodiments, the inner stent 938 or scaffold (also described herein as a luminal segment of a plurality of tethers) may comprise or be formed of a high-tensile microfilament. Exemplary, non-limiting examples of microfilament materials include polylactic acid, polyurethane, polyvinyl alcohol, polyethylene terephthalate, ceramics, and the like.

The stents 900, 938 described herein may have a form and/or structure that varies along the longitudinal axis L. For example, the strut members 904 may form a mesh-like or lattice structure. The strut members 904 may be interconnected in such a way as to form a shaped pattern of cells 902. The cells 902 may be open cells or closed cells. Example cell shapes may include, but are not limited to diamond, square, rectangle, triangle, oval, ganglion, or any combination thereof. In some examples, the cells may be evenly shaped and distributed from a first end of the stent to a second end of the stent. In some examples, the cells may include a number of strut members interconnected in such a way that when the stent expands radially, one or more of the cells become longitudinally shorter (relative to longitudinal axis L). Similarly, when the stent constricts radially, one or more of the cells become longitudinally longer (relative to longitudinal axis L).

In some embodiments, as shown in FIG. 9B, the plurality of tethers 922 includes a plurality of segments of portions. The plurality of tethers 922 may include a proximal plurality of tethers 932; a luminal segment 938 of the plurality of tethers 922 that forms an inner stent or support structure (that is disposed within a lumen 909 of the outer stent 900, as shown in FIG. 9A); and a distal plurality of tethers 934. The proximal plurality of tethers 932 radially extend from a distal side 913 of the proximal hub 924*a*. The distal plurality of tethers 934 radially extend from a proximal side 925 of the distal hub 924*b*. A proximal interface 935 between the proximal plurality of tethers 932 and the luminal segment 938 may be coupled to a proximal end 905 of the outer stent 900, shown in FIG. 9A. A distal interface 937 between the distal plurality of tethers 934 and the luminal segment 938 may be coupled to a distal end 907 of the outer stent, shown in FIG. 9A. Further, the luminal segment 938 may be coupled to the outer stent 900 at a plurality of fusion points (i.e., points at which fusion may occur once energy is applied), as shown in FIGS. 13A-14.

The luminal segment 938 may form an inner stent or support structure that is disposed in a lumen 909 of the outer stent 900. In some embodiments, one or more portions of the plurality of tethers 922 may be comprise a different material, a different or variable thickness, and/or have a different material property such that the plurality of tethers 922 are severable at the one or more portions. Additionally, or alternatively, in some embodiments, one or more portions of the plurality of tethers 922 may be selectively insulated, such that the plurality of tethers 922 can conduct an electric current. For example, fused portions (e.g., of the luminal segment 938) of the plurality of tethers 922 may include thicknesses, material properties, and/or insulation that allow fusion between the plurality of tethers 922 and the outer stent 900 without disengaging the plurality of tethers 922 from the proximal interface 935 and distal interface 937. Additionally, disengaging portions (e.g., proximal and distal portions 932, 934 of the plurality of tethers 922) of the plurality of tethers 922 may include different thicknesses, material properties, and/or insulation (from the fused portions of the plurality of tethers 922) that allow severability of the fused device from the proximal interface 935 and the distal interface 937 while preventing or minimizing disengagement or disruption of the fused portions. However, in some embodiments, the fused portions and disengaging portions may include the same thicknesses, material properties, and/or insulation to allow fusion without disengaging and disengagement without disrupting the fusion portions upon application of one or more pulses of electric current. In some embodiments, fusion and disengagement occur sequentially. In some embodiments, fusion and disengagement occur substantially simultaneously. Further, application of an electric current to the plurality of tethers 922 may dissociate or disengage the intravascular device from the proximal hub 924*a* and distal hub 924*b* and fuse the luminal segment 938 of the plurality of tethers 922 (also described herein as an inner stent or support structure) to the outer stent 900 of the intravascular device. Said another way, the electric current supplied by the input device may break the bonds at the proximal interface 935 and the distal interface 937 to release the intravascular device from the delivery system. For example, a composition and/or insulation of the plurality of tethers at the proximal interface 935 and distal interface 937 may be different or change such that application of an electric current breaks or dissociates the plurality of tethers at the proximal interface 935 and the distal interface 937. For example, there may be no insulation on the plurality of tethers at the proximal interface 935 and distal interface 937 so that an application of energy breaks or dissociates the plurality of tethers at the proximal interface 935 and the distal interface 937. For example, the composition of the plurality of tethers at the proximal interface 935 and distal interface may be a platinum-tungsten (PtW) alloy wire or may be made of, formed of, or other comprise other materials, such as silver, silver chloride, copper, platinum, chromium, aluminum, titanium, and nickel either in their pure form or as a combination so that an application of energy breaks or dissociates the plurality of tethers at the proximal interface 935 and the distal interface 937. Once broken, the delivery system (e.g., proximal and distal plurality of tethers 932, 934, respectively; hubs 924*a*, 924*b*; and translatable wire) can be removed from the patient, leaving the outer stent with fused inner stent (i.e., intravascular device).

Figure 10:
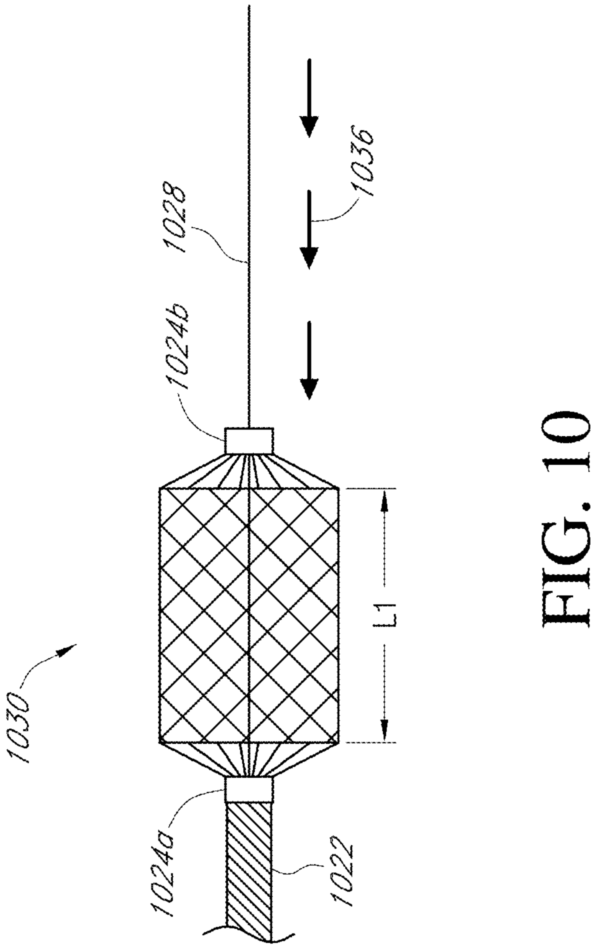
FIG. 10 shows a zoomed-in view of an embodiment of an expanded intravascular device, the intravascular device being expanded, at least in part, by proximal retraction of a translatable wire of a delivery system.
Figure 11:
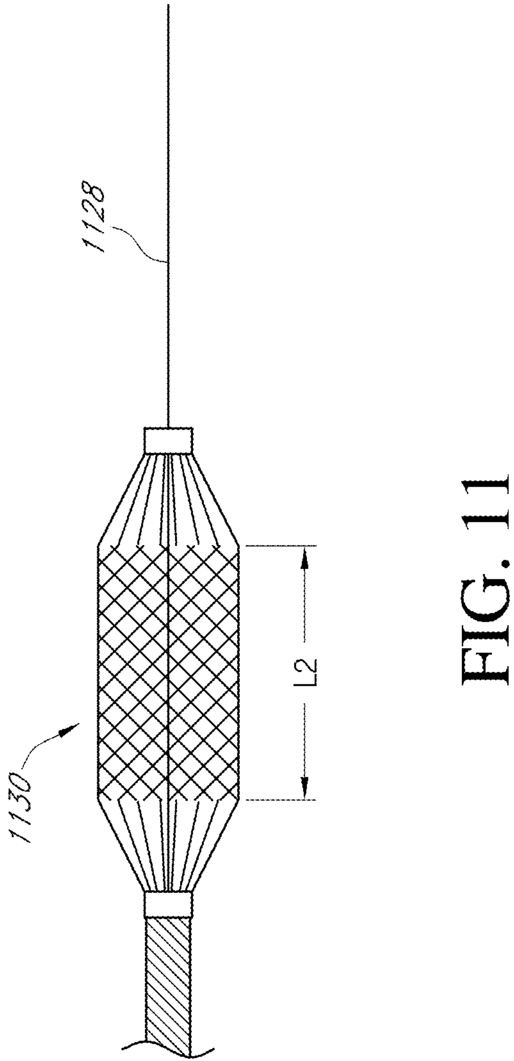
FIG. 11 shows a zoomed-in view of an embodiment of an expanded intravascular device, tethered to a delivery system.
Figure 12:
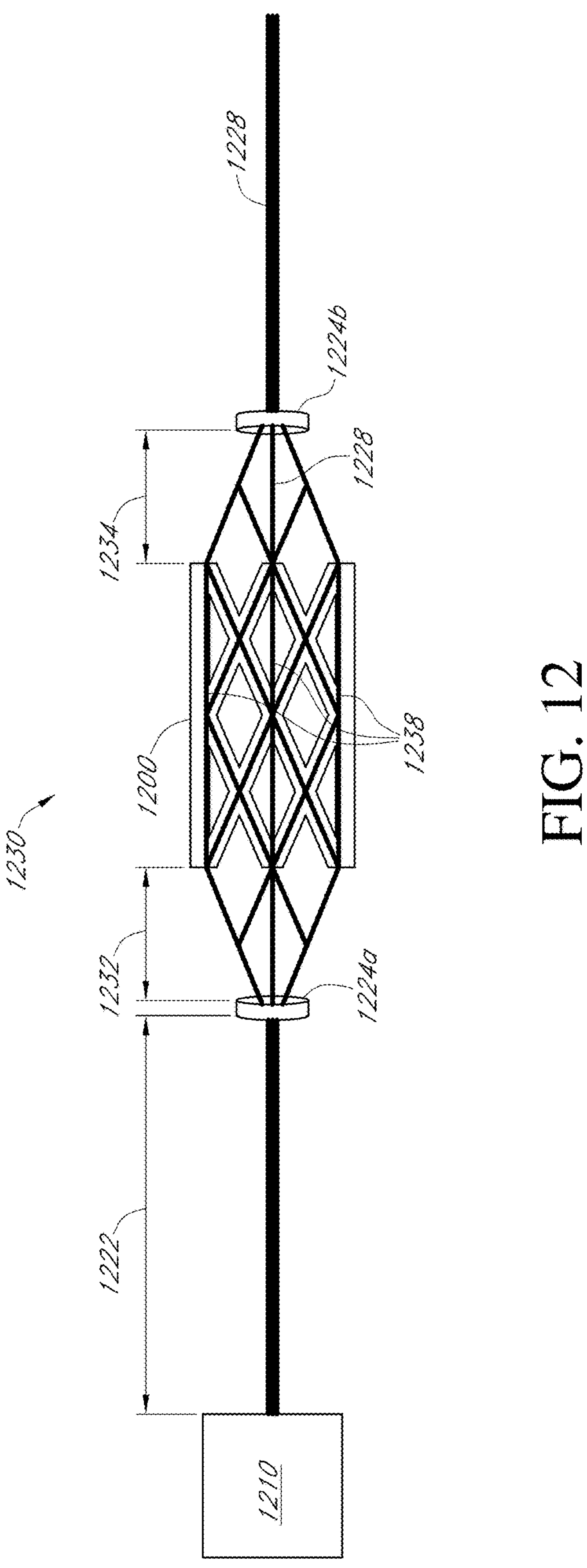
FIG. 12 shows a cross-sectional view of an embodiment of an intravascular device and portions of a delivery system.

FIG. 10 shows a zoomed-in view of an expanded intravascular device 1030. The intravascular device 1030 is shown in an expanded configuration achieved, at least in part, by proximal retraction of a translatable wire 1028 of a delivery system. The delivery system includes a translatable wire 1028 having an axially translatable (along translatable wire 1028) proximal hub 1024*a* and a fixed position distal hub 1024*b*. A plurality of tethers 1022 (e.g., braided tethers as shown in FIG. 8A) may couple the input device to the proximal hub 1024*a*, such that axial translation of the proximal hub 1024*a* causes longitudinal compression (at least partial compression) or at least partial decompression (along longitudinal axis L shown in FIG. 9A) of the plurality of tethers 1022. The plurality of tethers 1022 may pass through the proximal hub 1024*a* (as shown in FIG. 8B) and couple to the proximal end of the intravascular device. The plurality of tethers 1022 may further extend through the intravascular device and couple the distal end of the intravascular device to the distal hub 1024*b*, as shown in FIGS. 9A-9B and 12. When the translatable wire 1028 is proximally retracted (shown by arrows 1036), the intravascular device 1030 is at least partially expanded. The at least partial expansion may cause circumferential expansion of the intravascular device 1030 and a shortening of the intravascular device, along longitudinal axis L, shown in FIG. 9A. The length L1 of the intravascular device 1030 may be adjusted (i.e., the expansion diameter may be adjusted) by further proximally retracting the translatable wire 1028 (causing a shortening of length L1) or distally extending the translatable wire 1028 (causing a lengthening of length L1). Distal extension of the translatable wire 1028 may result in an increased length or reduced diameter of the intravascular device. FIG. 11 shows an intravascular device 1130 having an increased length L2 due to distal extension or pushing of the translatable wire 1128 distally. Intravascular device 1130 may have increased length L2, relative to length L1, due to less proximal retraction of the translatable wire 1128, as compared to the amount of proximal retraction of the translatable wire 1028 shown in FIG. 10.

FIG. 12 shows a cross-sectional view of an intravascular device 1230 and portions of a delivery system. FIG. 12 may be an assembled or combined view of the outer stent of FIG. 9A with the luminal segment of FIG. 9B. The intravascular device 1230 may include an outer stent 1200 having an outer stent lumen; and an inner scaffold (also described herein as the luminal segment 1238 of the plurality of tethers) disposed in the outer stent lumen. A plurality of tethers 1222 can extend from the input device 1210 and pass through the proximal hub 1224*a*. Proximal to the proximal hub 1224*a*, the plurality of tethers 1222 can be in a wound configuration or may form a coiled segment. Distal to the proximal hub 1224*a*, the plurality of tethers, described herein as the proximal plurality of tethers 1232, may be in an unwound configuration and coupled to a proximal end of the outer stent 1200. The proximal plurality of tethers 1232 may transition to a luminal segment 1238 of the plurality of tethers or also described herein as a scaffold that may extend through the outer stent lumen. The luminal segment 1238 of the plurality of tethers may be coupled to a luminal surface of the outer stent at a plurality of fusion contacts, such that the luminal segment 1238 of the plurality of tethers may exert a force on the outer stent to expand or contract the outer stent, responsive to manipulation of the translatable wire 1228 by the input device 1210. In some embodiments, the plurality of tethers 1222, 1232, 1234 that make up the luminal segment 1238 may be substantially parallel to one another in the lumen of the outer stent 1200. The luminal segment 1238 may transition to a distal plurality of tethers 1234 that are coupled to the distal hub 1224*b*.

The translatable wire 1228 may extend from the input device 1210, through a lumen formed by the wound or coiled plurality of tethers 1222, through the proximal hub 1224*a* (which may be slidably engaged with the translatable wire 1228), through the outer stent lumen, and be coupled to the distal hub 1224*b*. The distal hub 1224*b* may be fixedly coupled to the translatable wire 1228 such that proximal retraction or pulling or distal pushing of the translatable wire 1228 also proximally retracts or pulls or distally pushes, respectively, the distal hub 1224*b*. In contrast, the proximal hub 1224*a* may be slidably coupled to the translatable wire 1228 such that proximal retraction or pulling or distal pushing of the translatable wire 1228 may not substantially alter a position of the proximal hub 1224*a*. Alternatively, the position of the proximal hub 1224*a* may be altered, for example, when the intravascular device 1230 is expanded to a substantially maximum diameter, such that the intravascular device 1230 and/or the proximal plurality of tethers 1232 may apply a force on the proximal hub 1224*a*, thereby compressing the plurality of tethers 1222, proximal to the proximal hub 1224*a*.

The plurality of tethers 1222, 1232, 1234 and a luminal segment 1238 of the plurality of tethers may be capable of conducting an electric current. Application of the electric current to the plurality of tethers 1222, 1232, 1234 and/or luminal segment 1238 may cause selective dissociation of the proximal plurality of tethers 1232 and distal plurality of tethers 1234 from the intravascular device 1230. Further, application of the electric current to the plurality of tethers 1222, 1232, 1234 and/or luminal segment 1238 may cause fusion, at the fusion contacts, of the luminal segment 1238 with the outer stent 1200. Fusion at the fusion contacts of the luminal segment 1238 may fix the diameter of the outer stent 1200, and therefore the intravascular device 1230, to the selected or desired diameter based on the manipulation (axially translation) of the translatable wire 1228.

FIG. 13A shows a planar, cross-sectional view of an outer stent 1200 of the expanded intravascular device 1230 with a plurality of tethers 1222 extending through the lumen 1231 of the outer stent 1200. The proximal or distal hub 1224 and translatable wire 1228 are also visible in this cross-sectional view. Further, the plurality of fusion contacts 1246*a* are shown, coupling each of the tethers 1222 to the outer stent 1200.

Figure 13B:
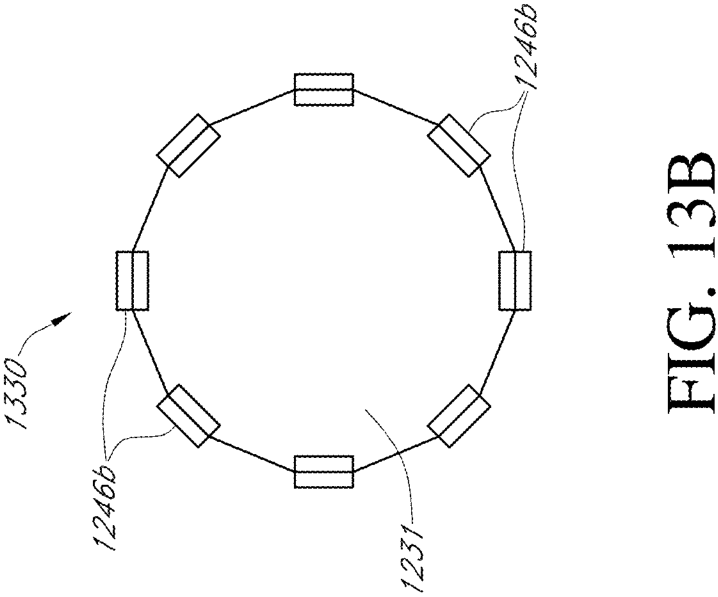
FIG. 13B shows a planar, cross-sectional view of an embodiment of the outer stent of FIG. 13A fused to the plurality of tethers of FIG. 13A after application of energy to the expanded intravascular device.
Figure 13A:
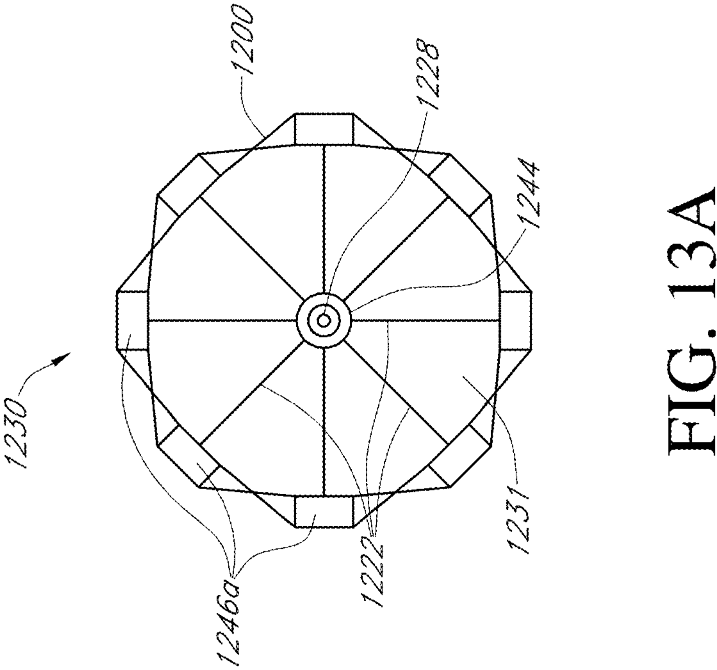
FIG. 13A shows a planar, cross-sectional view of an embodiment of an outer stent of an expanded intravascular device with a plurality of tethers extending through the lumen of the outer stent.
Figure 14:
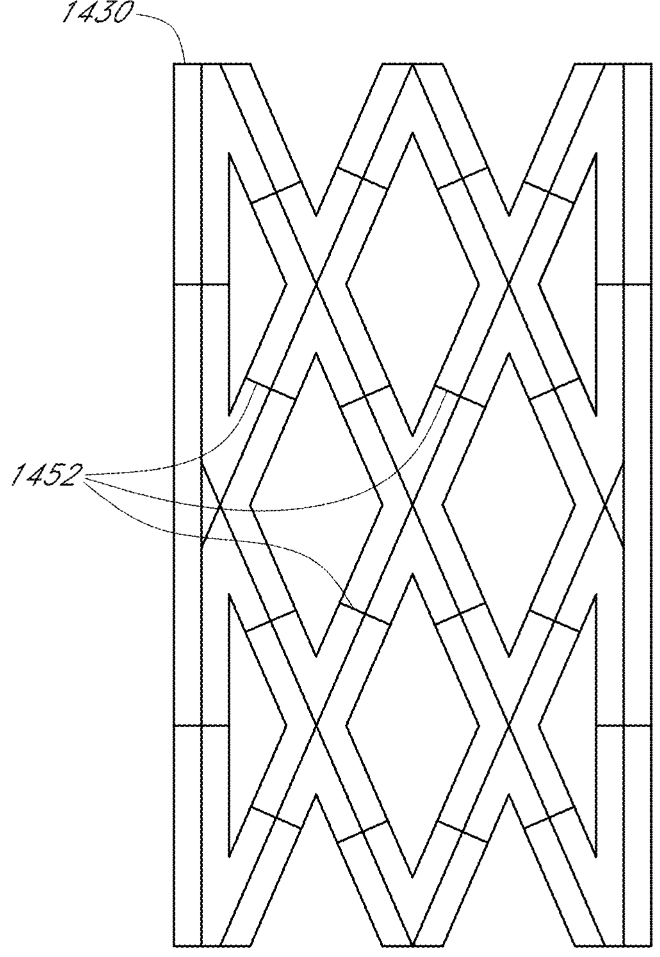
FIG. 14 shows an embodiment of one or more fusion points between an outer stent and an inner stent (or luminal segment of the plurality of tethers) of the expanded intravascular device after application of energy to the expanded intravascular device.

FIG. 13B shows a planar, cross-sectional view of the outer stent 1200 of FIG. 13A fused, at a plurality of fused contacts 1246*b* (i.e., the fusion having already occurred), to the plurality of tethers 1222 after application of energy to the intravascular device 1230. After fusion and removal of the translatable wire 1228 and remaining tethers, the lumen 1231 of the intravascular device 1230 is substantially clear of obstructions and that provide for a lumen that is held by sufficient radial strength to prevent vessel closure, allow sufficient blood flow therethrough, etc.

A zoomed-in view of a portion of the intravascular device 1430 having a plurality of fusion contacts 1452 is shown in FIG. 14. The fusion contacts 1452 may include, be formed of, or comprise uninsulated material (or bare material) and/or a composition that is sensitive to melting, polymerizing, disrupting, bonding, welding, etc. For example, the fusion contacts 1452 may each include a dot, a spot, a patch, or otherwise daub of a meltable composition, for example a polymer, that may fuse or melt into the lumen of the outer stent when the energy is applied. In some embodiments, this fusing may be a type of spot welding that can reinforce the structural integrity of the outer stent in its expanded position or configuration. Additionally, or alternatively, the fusion process may create sufficient radial strength to prevent vessel closure, for example due to plaque or other obstructions.

In the examples described herein, the number of fusion contacts (e.g., fusion contacts 1246*a*, fused contacts 1246*b*, fusion contacts 1452, etc.) may vary from about 3 fusion contacts to about 20 fusion contacts, about 5 fusion contacts to about 15 fusion contacts, about 4 fusion contacts to about 12 fusion contacts, etc. In some embodiments, instead of individual fusion contacts, a portion of or the entire outer stent may include, be formed of, or otherwise comprise a material that can fuse with the luminal segment of the plurality of tethers.

Figure 15:
FIG. 15 shows a flow chart of an embodiment of a method of deploying any of the intravascular devices described herein.
Figure 15:
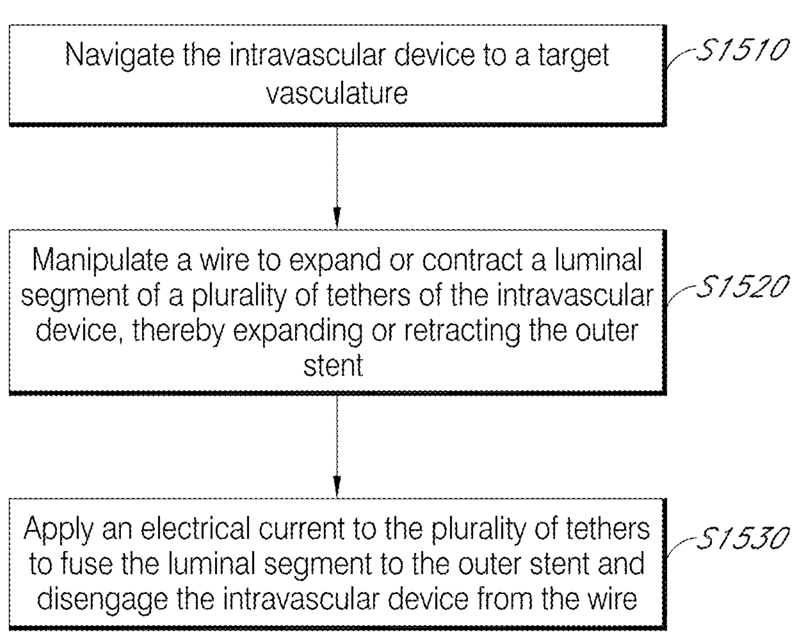

FIG. 15 shows a flow chart of an embodiment of a method 1500 for deploying an intravascular device. The method 1500 may include: navigating the intravascular device to a target vasculature at block S1510, for example any of the intravascular devices shown and/or described herein; manipulating a wire to expand or contract a luminal segment of a plurality of tethers of the intravascular device, thereby expanding or retracting the outer stent at block S1520; and applying an electric current to the plurality of tethers to fuse the luminal segment to the outer stent and disengage the intravascular device from the wire at block S1530.

The method 1500 may function to treat vascular abnormalities. In some embodiments, the method 1500 is a method of treatment to treat intracranial atherosclerosis. In some embodiments, the method 1500 is a method of treatment to treat carotid artery stenosis. In some embodiments, the method 1500 is a method of treatment to treat any vascular abnormality, intracranially, peripherally, or otherwise. The method 1500 may be used for vascular interventions, but can additionally, or alternatively, be used for any suitable applications, clinical or otherwise.

As shown in FIG. 15, an embodiment of a method 1500 for deploying an intravascular device includes block S1510, which recites navigating the intravascular device to a target vasculature. Navigating may include accessing a femoral artery, radial artery, or brachial artery using an access system (e.g., any combination of one or more of: an introducer, a long sheath, a guidewire, an insert catheter, or an access catheter). Navigating may include advancing one or more devices of the access system to achieve supra-aortic access. Navigating may include advancing one or more devices of the access system to achieve intracranial access. The target vasculature may include, but not be limited to: an internal carotid artery, a basilar artery, a right middle cerebral artery, a left middle cerebral artery, an intracranial vertebral artery, or a common carotid artery. Alternatively, the target vasculature may include a vessel in the peripheral vasculature. Alternatively, the target vasculature may include a peripheral artery.

The intravascular devices described herein and for use in method 1500 may include an outer stent having an outer stent lumen and an inner stent. The inner stent may be coupled, upon an application of electric energy, to the outer stent and disposed in the outer stent lumen. The delivery system may include one or more tethers or a plurality of tethers that extend through the outer stent lumen and form the inner stent. The tether may have electrical conductivity, such that electric current can be applied to the tethers to dissociate the intravascular device from the tethers and fuse the inner stent (luminal segment of tethers) to the outer stent of the intravascular device.

The intravascular devices described herein and for use in method 1500 may include a lumen having a first configuration during deployment, the first configuration having a first radial strength; and a second configuration after the deployment, the second configuration having a second radial strength, The intravascular devices described herein and for use in method 1500 may include a stent having a proximal end, a distal end, and a lumen therethrough; a wire extending through the lumen and for expanding or contracting the stent responsive to manipulation of the wire; a proximal hub slidably coupled to a proximal region of the wire; a distal hub coupled to a distal region of the wire; and a plurality of tethers extending from an input device to the proximal hub and to the proximal end of the stent. The plurality of tethers may extend through the lumen and couple the distal end of the stent to the distal hub. Further, at least a portion of the plurality of tethers may have electrical conductivity, such that application of an electric current to the at least a portion of the plurality of tethers may disengage the plurality of tethers from the proximal end and the distal end of the outer stent, respectively, and fuse a luminal segment of the plurality of tethers, extending through the lumen of the stent, to the stent.

As shown in FIG. 15, an embodiment of a method 1500 for deploying an intravascular device includes block S1520, which recites manipulating a wire to expand or contract a luminal segment of a plurality of tethers of the intravascular device, thereby expanding or retracting the outer stent. As described elsewhere herein, the luminal segment of the plurality of tethers may extend from the proximal hub, through the lumen of the outer stent, and couple to the distal hub. The luminal segment may be selectively coupled to the outer stent along its length. In some embodiments, manipulating the translatable wire may include axially translating the translatable wire. Manipulating the translatable wire may include proximal retracting the translatable wire to expand the inner stent and thereby the outer stent. Manipulating the translatable wire may include pushing distally the translatable wire to contract (e.g., unexpanded, reduce a diameter of, etc.) the inner stent and thereby the outer stent. The translatable wire may be manipulated by an input device, for example having an input element that is selectable by a user. Selection of the input element may cause the translatable wire to be advanced or retracted and/or locked at one or more positions, for example, once a desired deployed diameter and/or a desired position in the target vasculature of the intravascular device is achieved.

As shown in FIG. 15, an embodiment of a method 1500 for deploying an intravascular device includes block S1530, which recites applying an electric current to the plurality of tethers to fuse the luminal segment to the outer stent and disengage the intravascular device from the wire. The electric current may be activated by selection of a switch on the input device to electrically connect the plurality of tethers to the power source. The plurality of tethers may each include select sections or portions that do not include insulation and/or are formed of a particular composition, such that current can be discharged at these sections or portions to break a bond between the plurality of tethers and the intravascular device and/or fuse the plurality of tethers to the outer stent of the intravascular device, for example to set a diameter of the intravascular device. For example, disengaging the inner stent from the wire between the proximal hub and the proximal interface and/or between the distal hub and the distal interface.

The method 1500 may further include retrieving the intravascular device. For example, the intravascular device may be retrieved to remove the intravascular device from the target vasculature or to reposition the intravascular device in the target vasculature. Retrieving may include partially retrieving the intravascular device, for example, partially contracting (e.g., unexpanding, reducing a diameter of, etc.) the intravascular device to reposition or adjust an expansion diameter of the intravascular device. The step of retrieving may occur before applying the electric current.

Figure 16:
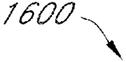
FIG. 16 shows a flow chart of an embodiment of a method of deploying any of the intravascular device described herein into an ophthalmic artery.
Figure 16:
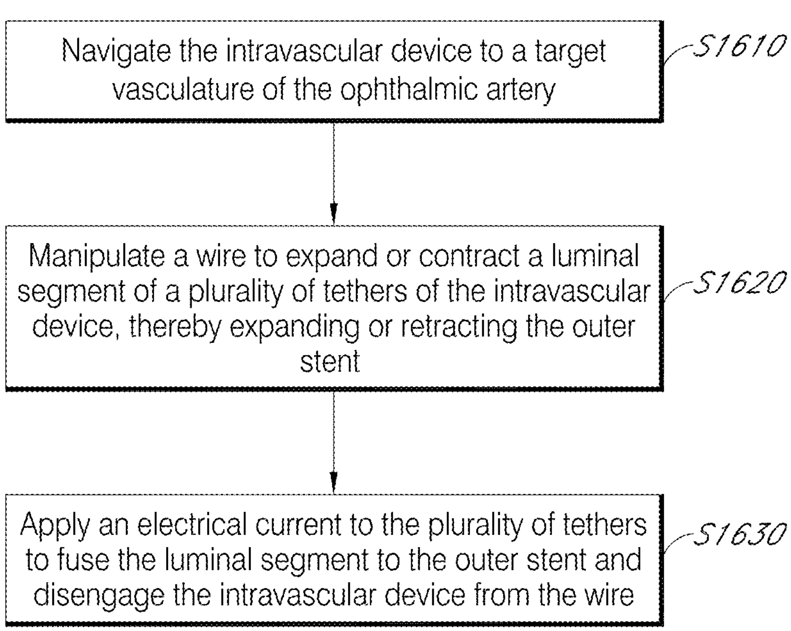

FIG. 16 shows a flow chart of an embodiment of a method 1600 for deploying an intravascular device into the ophthalmic artery, i.e., the first branch of the carotid artery. The method 1600 may include: navigating the intravascular device to a target branch of the ophthalmic artery at block S1610, for example any of the intravascular devices shown and/or described herein; manipulating a wire to expand or contract a luminal segment of a plurality of tethers of the intravascular device, thereby expanding or retracting the outer stent at block S1620; and applying an electric current to the plurality of tethers to fuse the luminal segment to the outer stent and disengage the intravascular device from the wire at block S1630.

As shown in FIG. 16, an embodiment of a method 1600 for deploying an intravascular device into the ophthalmic artery includes block 1610 which recites navigating the intravascular device to a target vasculature of the ophthalmic artery. Navigating may include accessing a femoral artery, radial artery, or brachial artery using an access system (e.g., any combination of one or more of: an introducer, a long sheath, a guidewire, an insert catheter, or an access catheter). Navigating may include advancing one or more devices of the access system to achieve supra-aortic access. Navigating may include advancing one or more devices of the access system to achieve ophthalmic artery access. Because of the acute angles of the branching and small lumen size of the ophthalmic artery, the intravascular devices described herein are capable of more efficiently navigating to the target vasculature of the ophthalmic artery due to the low radial strength of the intravascular devices described herein prior to fusion.

The intravascular devices described herein and for use in method 1600 may include an outer stent having an outer stent lumen and an inner stent. The inner stent may be coupled, upon an application of electric energy, to the outer stent and disposed in the outer stent lumen. The delivery system may include one or more tethers or a plurality of tethers that extend through the outer stent lumen and form the inner stent. The tether may have electrical conductivity, such that electric current can be applied to the tethers to dissociate the intravascular device from the tethers and fuse the inner stent (luminal segment of tethers) to the outer stent of the intravascular device. The flexibility of the outer stent and later support by the inner stent when placed at the target vasculature of the ophthalmic artery provides greater navigability and capability to adapt to the required radial strength for the target vasculature.

As shown in FIG. 16, an embodiment of a method 1600 for deploying an intravascular device includes block S1620, which recites manipulating a wire to expand or contract a luminal segment of a plurality of tethers (of the inner stent) of the intravascular device, thereby expanding or retracting the outer stent. As described elsewhere herein, the luminal segment of the plurality of tethers may extend from the proximal hub, through the lumen of the outer stent, and couple to the distal hub. The luminal segment may be selectively coupled to the outer stent along its length or at one or more locations along its length. In some embodiments, manipulating the translatable wire may include axially translating the translatable wire. Manipulating the translatable wire may include proximally retracting the translatable wire to expand the inner stent and thereby the outer stent. Manipulating the translatable wire may include pushing distally the translatable wire to contract (e.g., unexpanded, reduce a diameter of, etc.) the inner stent and thereby the outer stent. The translatable wire may be manipulated by an input device, for example having an input element that is selectable by a user. Selection of the input element may cause the translatable wire to be advanced or retracted and/or locked at one or more positions, for example, once a desired deployed diameter and/or a desired position in the target vasculature of the intravascular device is achieved. In other words, the intravascular device is capable of adapting to the target vasculature (e.g., tortuosity, size, etc.) of the ophthalmic artery.

As shown in FIG. 16, an embodiment of a method 1600 for deploying an intravascular device includes block S1630, which recites applying an electric current to the plurality of tethers to fuse the luminal segment to the outer stent and disengage the intravascular device from the wire. The electric current may be activated by selection of a switch on the input device to electrically connect the plurality of tethers to the power source. The plurality of tethers may each include select sections or portions that do not include insulation and/or are formed of a particular composition, such that current can be discharged at these sections or portions to break a bond between the plurality of tethers and the intravascular device and/or fuse the plurality of tethers to the outer stent of the intravascular device, for example to set a diameter of the intravascular device.

Figure 17:
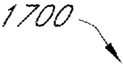
FIG. 17 shows a flow chart of an embodiment of a method of deploying any of the intravascular device described herein to support treatment of an aneurysm utilizing endovascular coiling.
Figure 17:
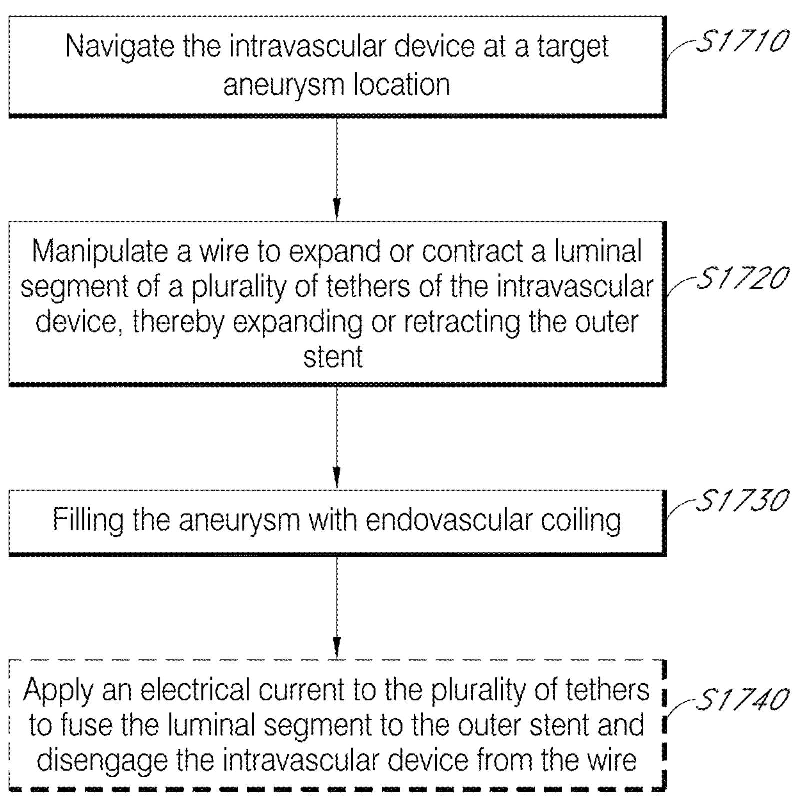

FIG. 17 shows a flow chart of an embodiment of a method 1700 for deploying an intravascular device at a neck of an aneurysm, for example, a wide neck of an aneurysm for Stent-Assisted Coiling (SAC) or Temporary Stent-Assisted Coiling (TSAC). The method 1700 may include: navigating the intravascular device to an aneurysm location at block S1710, for example any of the intravascular devices shown and/or described herein; manipulating a wire to expand or contract a luminal segment of a plurality of tethers of the intravascular device across a neck of the aneurysm, thereby expanding or retracting the outer stent at block S1720; filling the aneurysm with endovascular coiling to embolize the aneurysm at block S1730; and optionally applying an electric current to the plurality of tethers to fuse the luminal segment to the outer stent and disengage the intravascular device from the wire (e.g., in SAC applications) at block S1740; or remove the intravascular device (e.g., in TSAC applications). The method may function to prevent coil herniation where the coils may easily push out into the parent artery. The intravascular device may act as a barrier to prevent coil herniation. The method may function to provide support for coils to allow for more stable and dense packing of coils within the aneurysm sac. The method may provide for improved aneurysm occlusion rates and a lower rate of recurrence.

As shown in FIG. 17, an embodiment of a method 1700 for deploying an intravascular device at a target aneurysm location includes block 1710 which recites navigating the intravascular device to a target aneurysm location. Navigating may include accessing a femoral artery, radial artery, or brachial artery using an access system (e.g., any combination of one or more of: an introducer, a long sheath, a guidewire, an insert catheter, or an access catheter). Navigating may include advancing one or more devices of the access system to achieve supra-aortic access. Navigating may include advancing one or more devices of the access system to achieve intracranial access. Navigating may include advancing one or more devices to be positionable across a neck of an aneurysm in a target anatomy. The target vasculature of the aneurysm location may include, but not be limited to: an internal carotid artery, a basilar artery, a right middle cerebral artery, a left middle cerebral artery, an intracranial vertebral artery, or a common carotid artery. Alternatively, the target vasculature may include a vessel in the peripheral vasculature. Alternatively, the target vasculature may include a peripheral artery.

The intravascular devices described herein and for use in method 1700 may include an outer stent having an outer stent lumen and an inner stent. The inner stent may be coupled, upon an application of electric energy, to the outer stent and disposed in the outer stent lumen. The delivery system may include one or more tethers or a plurality of tethers that extend through the outer stent lumen and form the inner stent. The tether may have electrical conductivity, such that electric current can be applied to the tethers to dissociate the intravascular device from the tethers and fuse the inner stent (luminal segment of tethers) to the outer stent of the intravascular device. The flexibility of the outer stent and later support by the inner stent when placed at the neck of an aneurysm provides greater navigability and capability to adapt to the required radial strength of the target vasculature. Further, the retrievability and/or repositionability of the intravascular devices described herein may improve TSAC procedures where the intravascular device may be ultimately removed. Both SAC and TSAC procedures may also benefit from the ability to recapture and reposition the devices described herein to achieve improved aneurysm neck coverage.

As shown in FIG. 17, an embodiment of a method 1700 for deploying an intravascular device includes block S1720, which recites manipulating a wire to expand or contract a luminal segment of a plurality of tethers (of the inner stent) of the intravascular device, thereby expanding or retracting the outer stent. As described elsewhere herein, the luminal segment of the plurality of tethers may extend from the proximal hub, through the lumen of the outer stent, and couple to the distal hub. The luminal segment may be selectively coupled to the outer stent along its length. In some embodiments, manipulating the translatable wire may include axially translating the translatable wire. Manipulating the translatable wire may include proximally retracting the translatable wire to expand the inner stent and thereby the outer stent. Manipulating the translatable wire may include pushing distally the translatable wire to contract (e.g., unexpanded, reduce a diameter of, etc.) the inner stent and thereby the outer stent. The translatable wire may be manipulated by an input device, for example having an input element that is selectable by a user. Selection of the input element may cause the translatable wire to be advanced or retracted and/or locked at one or more positions, for example, once a desired deployed diameter and/or a desired position at the target aneurysm location of the intravascular device is achieved.

As shown in FIG. 17, an embodiment of a method 1700 for deploying an intravascular device includes block S1730, which recites filling the aneurysm with endovascular coiling to embolize the aneurysm. Although the intravascular device is in place, because of the flexibility of the intravascular device, the endovascular coiling may be introduced to the aneurysm prior to fixing the intravascular device in across the neck of the aneurysm. Once filled, to reduce the likelihood of prolapse, the intravascular device is fixed in place to further support the endovascular coiling in SAC procedures or recaptured a removed in TSAC procedures. In some embodiments, the endovascular coiling may be introduced to the aneurysm after deployment of the intravascular device at the neck of the aneurysm.

As shown in FIG. 17, an embodiment of a method 1700 for deploying an intravascular device includes block S1740, which recites applying an electric current to the plurality of tethers to fuse the luminal segment to the outer stent and disengage the intravascular device from the wire. The electric current may be activated by selection of a switch on the input device to electrically connect the plurality of tethers to the power source. The plurality of tethers may each include select sections or portions that do not include insulation and/or are formed of a particular composition, such that current can be discharged at these sections or portions to break a bond between the plurality of tethers and the intravascular device and/or fuse the plurality of tethers to the outer stent of the intravascular device, for example to set a diameter of the intravascular device and prevent prolapse of the endovascular coiling.

PROPHETIC EXAMPLE

A balloon-expandable stent, self-expandable stent, outer stent alone (e.g., FIG. 9A), and fused outer stent and inner stent (e.g., cross-sectional view in FIG. 13B) may undergo radial strength testing. The radial strength may be determined by compressing, between two plates of a load machine, each device to 50% of its expanded diameter. Using a load machine, the radial strength (in Newton, N) of each of the stents may be determined as shown below in Table 1.

TABLE 1

Prophetic Radial strength Measurements

| Stent | Prophetic Radial strength |
|---|---|
| Balloon expandable stent | About 13N to about 15N |
| Self-expanding stent | About 0.14N to about 0.20N |
| Outer stent | About 0N to about 0.5N |
| Fused outer and inner stents | About 1.0N to about 3.0N |

When comparing balloon-expandable and self-expandable stents vs. the outer stent alone and the fused outer and inner stents, the balloon expandable stent and the self-expanding stent had a much higher radial strength. The outer stent alone had a very low radial strength. The fused outer and inner stent had a tunable radial strength, such that its radial strength was between that of the outer stent alone and the balloon-expandable stent or the self-expandable stent.

EXAMPLES

Example 1. An intravascular device comprising: an outer stent and a support structure that is at least partially disposed in a lumen of the outer stent, the lumen is configured to have: a first configuration during deployment, wherein the first configuration has a first radial strength; and a second configuration after the deployment, wherein the second configuration has a second radial strength and the support structure is fused, at a plurality of fusion points, to the lumen of the outer stent by applying energy to the intravascular device, the fusion fixing a diameter of the intravascular device in the second configuration, wherein the first radial strength is less than the second radial strength.

Example 2. The intravascular device of example 1, wherein the intravascular device is configured for insertion within an intracranial vessel.

Example 3. The intravascular device of any of the preceding examples, but particularly example 1, further comprising: a wire configured to extend through the lumen and expand or contract the outer stent responsive to manipulation of the wire; a proximal hub slidably coupled to a proximal region of the wire; and a distal hub coupled to a distal region of the wire; wherein: the support structure comprises a plurality of tethers configured to extend from an input device to the proximal hub and to a proximal end of the outer stent, the plurality of tethers is further configured to extend through the lumen and couple a distal end of the outer stent to the distal hub, and at least a portion of the plurality of tethers has electrical conductivity; application of an electric current to the at least a portion of the plurality of tethers is configured to: disengage the plurality of tethers from a proximal end and a distal end of the outer stent, respectively, for removal of the wire, and fuse a luminal segment of the plurality of tethers, extending through the lumen of the outer stent, to the lumen of the outer stent.

Example 4. The intravascular device of any of the preceding examples, but particularly example 1, wherein the outer stent comprises a polymer.

Example 5. The intravascular device of any of the preceding examples, but particularly example 3, wherein each of the plurality of tethers comprises a braided wire.

Example 6. The intravascular device of any of the preceding examples, but particularly example 3, wherein the plurality of tethers each comprise a plurality of segments.

Example 7. The intravascular device of any of the preceding examples, but particularly example 6, wherein a coiled segment of the plurality of tethers is configured to extend from the input device to the proximal hub.

Example 8. The intravascular device of any of the preceding examples, but particularly example 7, wherein a proximal segment of each of the plurality of tethers is configured to extend from the proximal hub to the proximal end of the outer stent.

Example 9. The intravascular device of any of the preceding examples, but particularly example 8, wherein the proximal hub is configured to slide along the wire relative to the distal hub to expand or contract the outer stent.

Example 10. The intravascular device of any of the preceding examples, but particularly example 8, wherein the coiled segment and the proximal segment are electrically conductive, such that the application of the electric current is configured to disengage the plurality of tethers from the proximal end of the outer stent.

Example 11. The intravascular device of any of the preceding examples, but particularly example 6, wherein the plurality of tethers is substantially parallel to each other in the luminal segment.

Example 12. The intravascular device of any of the preceding examples, but particularly example 6, wherein a distal segment of each of the plurality of tethers is configured to extend from the distal end of the outer stent to the distal hub.

Example 13. The intravascular device of any of the preceding examples, but particularly example 12, wherein the distal segment is electrically conductive, such that the application of the electric current is configured to disengage the plurality of tethers from the distal end of the outer stent.

Example 14. The intravascular device of any of the preceding examples, but particularly example 3, wherein the luminal segment of the plurality of tethers comprises a plurality of fusion contacts configured to fuse the luminal segment of the plurality of tethers to the lumen of the outer stent upon application of the electric current.

Example 15. The intravascular device of any of the preceding examples, but particularly example 3, wherein the luminal segment of the plurality of tethers comprises uninsulated material.

Example 16. The intravascular device of any of the preceding examples, but particularly example 3, further comprising the input device coupled to a proximal end of the plurality of tethers.

Example 17. A method of deploying an intravascular device, comprising: navigating the intravascular device to a target vasculature, the intravascular device comprising: an outer stent having an outer stent lumen, a support structure extending through the outer stent lumen, and a translatable wire configured to extend through the outer stent lumen and couple to the support structure; manipulating the translatable wire to cause the support structure to at least partially expand or contract the outer stent; and applying an electric current to the support structure to fuse at least a portion of the support structure to the outer stent at a plurality of fusion points along the outer stent lumen and to disengage the support structure from the translatable wire.

Example 18. The method of example 17, further comprising retrieving, at least partially, the intravascular device before applying the electric current.

Example 19. The method of any of the preceding examples, but particularly example 17, wherein, before fusion, the outer stent has a first radial strength that is less than a second radial strength of the outer stent after fusion to the support structure.

Example 20. The method of any of the preceding examples, but particularly example 17, wherein the deploying of the intravascular device is for treating intracranial atherosclerosis disease in the target vasculature of a patient.

Although the various embodiments described herein include an inner stent and an outer stent, it is also contemplated herein that various embodiments could include a single polymer stent that is flexible and thin to allow the device to reach distal lesions through tortuous vasculature. The polymer stent could be expanded as the distal and proximal ends are brought closer to each other (e.g., using proximal retraction of the translatable wire) and could also be unexpanded as the distal and proximal ends are pulled in the opposite direction (e.g., using distal pushing of the translatable wire). Manipulation of the translatable wire, resulting in expansion or contraction of the polymer stent, may enable a plurality of trials to achieve the desired location and/or expansion diameter.

References in the specification to "one embodiment," "an embodiment," "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

As used in the description and claims, the singular form "a", "an" and "the" include both singular and plural references unless the context clearly dictates otherwise. For example, the term "tether" may include, and is contemplated to include, a plurality of tethers. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intravascular device comprising:

an outer stent and an inner stent that is at least partially disposed in a lumen of the outer stent, wherein the lumen is configured to have:

a first configuration during deployment, wherein the first configuration has a first radial strength; and a second configuration after the deployment, wherein the second configuration has a second radial strength and the inner stent is fused, at a plurality of fusion points, to the lumen of the outer stent by applying energy to the intravascular device, the fusion fixing a selected diameter of the intravascular device in the second configuration after the deployment, wherein the energy is selected from an electric current, a heat, and an ultrasonic energy; and wherein the selected diameter is adjusted in-situ, and wherein the first radial strength is less than the second radial strength.

2. The intravascular device of claim 1, wherein the intravascular device is configured for insertion within an intracranial vessel.

3. The intravascular device of claim 1, further comprising:

a wire configured to extend through the lumen and expand or contract the outer stent responsive to manipulation of the wire;

a proximal hub slidably coupled to a proximal region of the wire; and a distal hub coupled to a distal region of the wire;

wherein:

the inner stent comprises a plurality of tethers configured to extend from an input device to the proximal hub and to a proximal end of the outer stent, the plurality of tethers is further configured to extend through the lumen and couple a distal end of the outer stent to the distal hub, and at least a portion of the plurality of tethers has electrical conductivity;

application of an electric current to the at least a portion of the plurality of tethers is configured to:

disengage the plurality of tethers from the proximal end and the distal end of the outer stent, respectively, for removal of the wire, and fuse a luminal segment of the plurality of tethers, extending through the lumen of the outer stent, to the lumen of the outer stent.

4. The intravascular device of claim 1, wherein the outer stent comprises a polymer.

5. The intravascular device of claim 3, wherein each of the plurality of tethers comprises a braided wire.

6. The intravascular device of claim 3, wherein the plurality of tethers each comprise a plurality of segments.

7. The intravascular device of claim 6, wherein a coiled segment of the plurality of tethers is configured to extend from the input device to the proximal hub.

8. The intravascular device of claim 7, wherein a proximal segment of each of the plurality of tethers is configured to extend from the proximal hub to the proximal end of the outer stent.

9. The intravascular device of claim 8, wherein the proximal hub is configured to slide along the wire relative to the distal hub to expand or contract the outer stent.

10. The intravascular device of claim 8, wherein the coiled segment and the proximal segment are electrically conductive, such that the application of the electric current is configured to disengage the plurality of tethers from the proximal end of the outer stent.

11. The intravascular device of claim 6, wherein the plurality of tethers is substantially parallel to each other in the luminal segment.

12. The intravascular device of claim 6, wherein a distal segment of each of the plurality of tethers is configured to extend from the distal end of the outer stent to the distal hub.

13. The intravascular device of claim 12, wherein the distal segment is electrically conductive, such that the application of the electric current is configured to disengage the plurality of tethers from the distal end of the outer stent.

14. The intravascular device of claim 3, wherein the luminal segment of the plurality of tethers comprises a plurality of fusion contacts configured to fuse the luminal segment of the plurality of tethers to the lumen of the outer stent upon application of the electric current.

15. The intravascular device of claim 3, wherein the luminal segment of the plurality of tethers comprises uninsulated material.

16. The intravascular device of claim 3, further comprising the input device coupled to a proximal end of the plurality of tethers.

17. An intravascular device comprising:

an outer stent; and an inner stent that is at least partially disposed in a lumen of the outer stent, wherein the outer stent and the inner stent are configured to have:

a first configuration during deployment, wherein the first configuration has a first radial strength; and a second configuration after the deployment, wherein the second configuration has a second radial strength and wherein the inner stent is fused to the lumen of the outer stent by applying energy to the intravascular device, the fusion fixing a deployed selected diameter of the intravascular device in the second configuration after the deployment, wherein the energy is selected from an electric current, a heat, and an ultrasonic energy, and wherein the first radial strength is less than the second radial strength.

18. The intravascular device of claim 17, wherein the selected diameter may be adjusted before the fusion.

19. The intravascular device of claim 18, wherein the energy comprises the electric current, and wherein the fusion comprises applying the electric current to the inner stent to fuse at least a portion of the inner stent to the outer stent at a plurality of fusion points along the lumen.

20. The intravascular device of claim 17, wherein the energy comprises the electric current, and wherein the fusion comprises applying the electric current to the inner stent to fuse at least a portion of the inner stent to the outer stent at a plurality of fusion points along the lumen and disengages the inner stent from a translatable wire configured to couple to the inner stent.

* * * * *